(12) United States Patent
Moraski et al.

(10) Patent No.: US 9,605,002 B2
(45) Date of Patent: Mar. 28, 2017

(54) 5,5-HETEROAROMATIC ANTI-INFECTIVE COMPOUNDS

(71) Applicant: UNIVERSITY OF NOTRE DAME DU LAC, Notre Dame, IN (US)

(72) Inventors: Garrett Moraski, Bozeman, MT (US); Marvin J. Miller, South Bend, IN (US)

(73) Assignee: UNIVERSITY OF NOTRE DAME DU LAC, South Bend, IN (US)

( * ) Notice: Subject to any disclaimer, the term of this patent is extended or adjusted under 35 U.S.C. 154(b) by 0 days.

(21) Appl. No.: 14/415,726

(22) PCT Filed: Jul. 18, 2013

(86) PCT No.: PCT/US2013/051125
§ 371 (c)(1),
(2) Date: Jan. 19, 2015

(87) PCT Pub. No.: WO2014/015167
PCT Pub. Date: Jan. 23, 2014

(65) Prior Publication Data
US 2015/0210715 A1  Jul. 30, 2015

Related U.S. Application Data

(60) Provisional application No. 61/672,968, filed on Jul. 18, 2012.

(51) Int. Cl.
| C07D 513/04 | (2006.01) |
| A61K 31/4188 | (2006.01) |
| A61K 9/00 | (2006.01) |
| A61K 9/20 | (2006.01) |
| A61K 9/28 | (2006.01) |

(52) U.S. Cl.
CPC .......... *C07D 513/04* (2013.01); *A61K 9/0014* (2013.01); *A61K 9/0019* (2013.01); *A61K 9/2059* (2013.01); *A61K 9/2866* (2013.01); *A61K 31/4188* (2013.01)

(58) Field of Classification Search
CPC .................. C07D 513/04; A61K 31/4188
See application file for complete search history.

(56) References Cited

U.S. PATENT DOCUMENTS

| 2010/0016401 A1* | 1/2010 | Aissaoui et al. ............ 514/412 |
| 2010/0152192 A1* | 6/2010 | Chaudhari et al. .......... 514/249 |
| 2010/0222600 A1* | 9/2010 | Aissaoui et al. ............ 548/950 |

FOREIGN PATENT DOCUMENTS

| FR | WO2008081399 | 7/2008 |
| FR | WO2008087611 | 7/2008 |
| GB | WO2009147431 | 12/2009 |
| WO | WO9529922 | 11/1995 |
| WO | WO2008020405 | 2/2008 |
| WO | WO2008038251 | 4/2008 |
| WO | WO2009016560 | 2/2009 |
| WO | WO2011073316 | 6/2011 |

OTHER PUBLICATIONS

Jan. 20, 2015, International Preliminary Report on Patentability issued in PCT/US13/051125.
Jan. 27, 2014, International Search Report issued in PCT/US13/051125.
Jan. 18, 2015, Written Opinion of the ISA issued in PCT/US13/051125.
Feb. 2, 2016, European Search Report issued in EP Application No. 13820038.1.
2003, Terzioglu, Nalan et al., "Synthesis and anticancer evaluation of some new hydrazone derivatives of 2,6-dimethylimidazo[2,1-b][1,3,4]thiadiazole-5-carbohydrazide", European Journal of Medicinal Chemistry, 2003, 38, pp. 781-786.
1984, Abignente E et al., Research on heterocyclic compounds, XVIII, Imidazo[2,1-b]-1,3,4-thiadiazole derivatives. II Farmaco, Edizione Scientifica, 1984, 40(3), pp. 190-1999.
1954, Syoichi, Ban et al., Studies on Chemotherapeutics, XXXIX. Synthesis of imidazo compounds. IV. Imidazo[2,1-b]thiadiazole derivatives. (2). Yakugaku Zasshi, 1954, 74, pp. 658-661, Table II.
Aug. 18, 2009, Odell, R. et al.,"Functionalized 3-amino-imidazo[1,2-a]pyridines: A novel class of drug-like Mycobacterium tuberculosis glutamine synthetase inhibitors", Bioorganic & Medicinal Chemistry Letters, Pergamon, Amsterdam, NL, vol. 19, No. 15, Aug. 15, 2009, pp. 4790-4793.
Jan. 18, 2016, Chinese Search Report issued in CN 2013800479946.
Jan. 26, 2016, Chinese Office Action issued in CN 2013800479946.

* cited by examiner

*Primary Examiner* — Rebecca Anderson
*Assistant Examiner* — Karen Cheng
(74) *Attorney, Agent, or Firm* — Neifeld IP Law, P.C.

(57) ABSTRACT

The invention provides a series of 5,5-heteroaromatic compounds, syntheses thereof, compositions thereof, and methods of using such compounds and compositions. Various embodiments provide methods of killing and/or inhibiting the growth of *M. tuberculosis* and/or *M. avium*, and methods of treating, preventing, and/or ameliorating *M. tuberculosis* and/or *M. avium* infections in a subject. In various embodiments, the 5,5-heteroaromatic compound is N-(4-(4-chlorophenoxy)benzyl)-2,6-dimethylimidazo[2,1-b]thiazole-5-carboxamide.

20 Claims, 1 Drawing Sheet

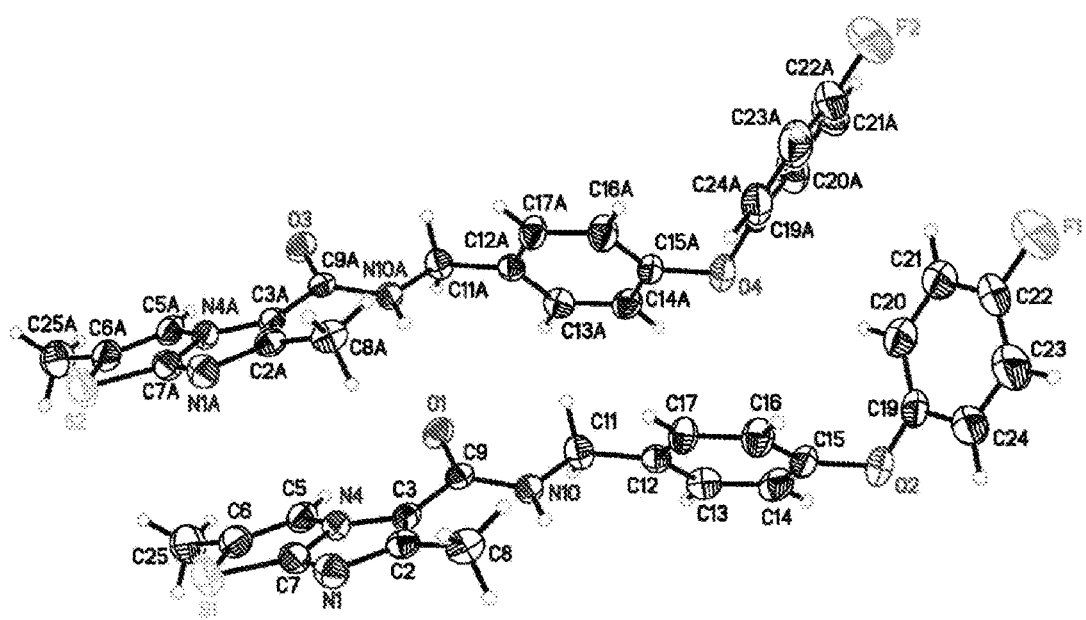

5,5-HETEROAROMATIC ANTI-INFECTIVE COMPOUNDS

RELATED APPLICATIONS

This application claims priority under 35 U.S.C. §119(e) to U.S. Provisional Patent Application No. 61/672,968, filed Jul. 18, 2012, which is incorporated herein by reference.

GOVERNMENT SUPPORT

This invention was made with government support under Grant No. R01 AI 054193 awarded by the National Institutes of Health. The United States Government has certain rights in the invention.

BACKGROUND OF THE INVENTION

The battle against tuberculosis (TB), caused by the bacterium *Mycobacterium tuberculosis* (Mtb), has raged for millennia. Throughout history, TB has claimed the lives of over one billion people and currently infects one third of the world's population. With 3.1 million deaths a year, TB, as a single causative agent, is the leading killer among infectious diseases. The spread of TB was significantly affected with the advent of several chemotherapy agents during the mid-1900s. However, since the 1980s, TB has been on the rise. Presently, 8 million new cases are added annually.

The increase in cases of TB/HIV co-infection and the spread of multiple-drug resistant TB (MDR-TB, strains that are resistant to first line drugs isoniazid and rifampin) and extensively drug resistant TB (XDR-TB, strains that are resistant to isoniazid and rifampin, as well as any fluoroquinolone and at least one of three injectable second-line drugs, such as amikacin, kanamycin, or capreomycin) are making matters worse. More than ever, there is an urgent need to develop new anti-TB drugs to combat the spread of TB, particularly in its hard-to-kill multidrug-resistant and latent forms.

SUMMARY

The invention provides a series of 5,5-heteroaromatic compounds, syntheses thereof, compositions thereof, and methods of using such compounds and compositions. Various embodiments provide methods of killing and/or inhibiting the growth of bacteria such as *M. tuberculosis* and/or *M. avium*, and certain resistant strains thereof. The invention also provides methods of treating, preventing, and/or ameliorating *M. tuberculosis* and/or *M. avium* infections in a subject.

Accordingly, the invention provides a compound of Formula (A):

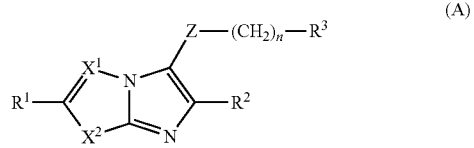

(A)

wherein $X^1$ is CH, $CR^4$, or N;

$X^2$ is S, sulfinyl (S(=O)), sulfonyl (S(=O)$_2$), $CH_2$, $CHR^1$, O, NH, or $NR^4$;

Z is —C(=O)NH—, —C(=O)O—, —C(=O)C (=O)—, —CH$_2$C(=O)—, —C(=O)CH$_2$—, or —NH—C(=O)NH—; and n is 0 to 4.

In the formulas described herein, the "R" groups (e.g., $R^1$, $R^2$, $R^3$, $R^4$, etc.) can be defined as the following:

$R^1$ is H, alkyl, cycloalkyl, heterocycle, alkoxy, aryl, heteroaryl, halo, or amine;

$R^2$ is H, alkyl, cycloalkyl, heterocycle, alkoxy, aryl, heteroaryl, halo, or amine;

$R^3$ is H, alkyl, alkoxy, amino, cycloalkyl, heterocycle, aryl, aryloxy, or heteroaryl; and each $R^4$ is independently H, alkyl, cycloalkyl, heterocycle, aryl, or heteroaryl;

wherein an alkyl, cycloalkyl, heterocycle, aryl, aryloxy, heteroaryl, alkoxy, or amine of $R^1$, $R^2$, $R^3$, or $R^4$ is optionally substituted with one to or more substituents, e.g., about one to about five, substituents. Any of the values of an R group above or described herein may also be excluded from a particular R group definition or formula of the claimed invention.

The invention also provides a pharmaceutically acceptable salt of any one or more of the formulas described herein.

In one embodiment, an alkyl, cycloalkyl, heterocycle, aryl, aryloxy, heteroaryl, alkoxy, or amine of an R groups (e.g., $R^1$, $R^2$, $R^3$, or $R^4$) can be unsubstituted, or alternatively, substituted with one to five substituents, such as one or more of ($C_1$-$C_6$)alkyl, ($C_1$-$C_6$)alkene, ($C_1$-$C_6$)alkyne, epoxide, oxo, alkyl carboxylate, alkoxy, carbaldehyde, halo, OH, CN, $NO_2$, or SH groups, or a combination thereof.

In some embodiments, n is 0.
In some embodiments, n is 1.
In some embodiments, n is 2.
In some embodiments, n is 3.
In some embodiments, n is 4.

In various embodiments, $R^3$ is phenyl, pyridyl, indolyl, dihydrobenzofuranyl, or benzo[d]oxazolyl, where each $R^3$ can be unsubstituted, or substituted as described herein.

In various embodiments, $R^3$ is phenyl or pyridyl substituted with one, two, or three alkyl, alkoxy, halo, trifluoromethyl, trifluoromethoxy, methylamino, dimethylamino, phenyl, phenyloxy, morpholino, thiomorpholino, piperazinyl, piperidinyl, imidazolyl, diazinyl, triazinyl, or pyrollidinyl groups.

In certain embodiments, $R^1$ is ($C_1$-$C_6$)alkyl, halo, or trifluoromethyl.

In certain embodiments, $R^2$ is ($C_1$-$C_6$)alkyl or trifluoromethyl.

In certain embodiments, $X^1$ is CH, $X^2$ is S, Z is —C(=O)NH—, or —C(=O)O—.

In certain embodiments, Z is —C(=O)NH—.
In certain embodiments, Z is —C(=O)O—.
In certain embodiments, Z is —C(=O)C(=O)—.
In certain embodiments, Z is —CH$_2$C(=O)—, —C(=O)CH$_2$—, or —NH—C(=O)NH—.

In certain embodiments, $R^1$ is methyl, trifluoromethyl, chloro, or fluoro.

In certain embodiments, $R^2$ is methyl, trifluoromethyl, or ethyl.

In certain embodiments, Z is —C(=O)NH—, n is 1-4, $R^1$ is methyl, trifluoromethyl, chloro, or fluoro, and $R^2$ is methyl, trifluoromethyl, or ethyl.

In various embodiments, for example, an embodiment having any combination of the elements described above or herein, $R^3$ can be:

(a) $OR^4$ or $NHR^4$;

(b)

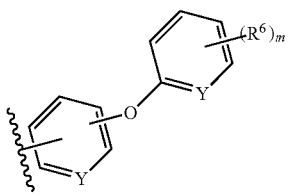
(Ib)

wherein each Y is independently CH or N; $R^6$ is H, $CF_3$, $OCF_3$, halo, methylsulfone, alkoxy, amine, or nitrile; and m is 1-4;

(c)

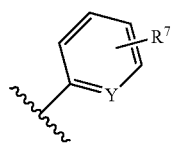
(Ic)

wherein Y is CH or N; and $R^7$ is a heterocycle, wherein the heterocycle is an optionally substituted furan, thiophene, imidazole, oxazole, oxazoline, oxadiazole, thiadiazole, thiazole, thiazoline, triazole, pyridine, pyrazine, pyrazole, diketopiperazine, quinoline, isoquinoline, or oxazolindinone;

(d)

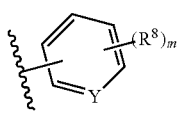
(Id)

wherein Y is CH or N; and $R^8$ is $CF_3$, $OCF_3$, halo, methylsulfone, nitrile, or optionally substituted alkoxy, amine, phenyl, or heterocycle; and m is 0-3;

(e)

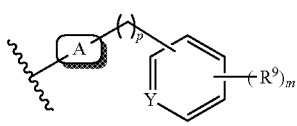
(Ie)

wherein A is a heterocycle, wherein the heterocycle is a furan, a thiophene, an imidazole, an oxazole, an oxazoline, an oxadiazole, a thiadiazole, a thiazole, a thiazoline, a triazole, a pyridine, a pyrazine, a diketopiperazine, a quinoline, an isoquinoline, a benzimidazole, a benzoxazole, a benzthiazole or an oxazolindinone; $R^9$ is $CF_3$, $OCF_3$, halo, methylsulfone, alkoxy, amine or nitrile; Y is CH or N; m is 0-5; and p is 0-4;

(f)

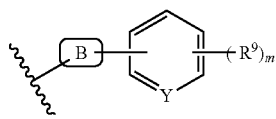
(If)

wherein B is a heterocycle, wherein the heterocycle is a piperazine or a piperidine; $R^9$ is $CF_3$, $OCF_3$, halo, methylsulfone, alkoxy, amine, or nitrile; Y is CH or N; and m is 0-4;

(g)

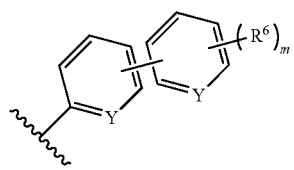
(Ig)

wherein each Y is independently CH or N; $R^6$ is $CF_3$, $OCF_3$, halo, methylsulfone, alkoxy, amine or nitrile; and m is 0-4; or (h)

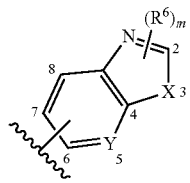
(Ih)

wherein the structure (Ih) is connected to the structure of Formula A at position 2, 6, or 7; $R^6$ when present is located at position 2, 6, or 7, or a combination thereof, provided that structure (Ih) is not connected to the structure of Formula A at the same position; X is $CH_2$, NH, $NR_4$, S, or O; Y is CH or N; $R^6$ is $CF_3$, $OCF_3$, halo, methylsulfone, alkoxy, amine or nitrile; and m is 0-3.

In one embodiment, the compound of Formula (A) is a compound of Formula (B):

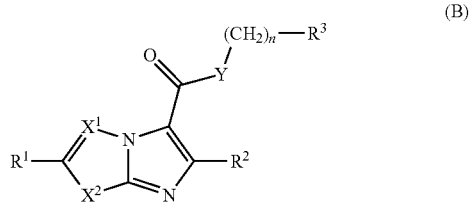
(B)

wherein Y is NH, O, or a direct bond; or a pharmaceutically acceptable salt thereof.

In another embodiment, the compound of Formula (B) is a compound of Formula (C):

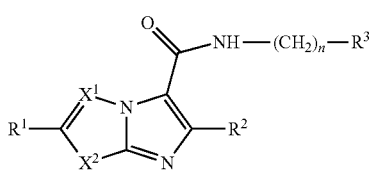

(C)

or a pharmaceutically acceptable salt thereof.

In yet another embodiment, the compound of Formula (B) is a compound of Formula (I):

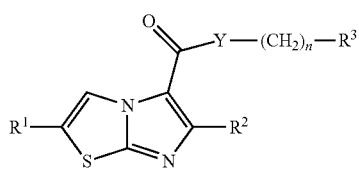

(I)

or a pharmaceutically acceptable salt thereof.

In an additional embodiment, the compound of Formula (I) is a compound of Formula (II):

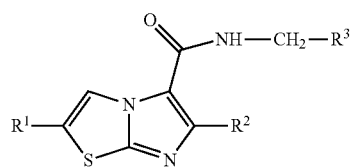

(II)

or a pharmaceutically acceptable salt thereof.

In certain embodiments of the formulas described above and herein, $R^2$ is alkyl or alkoxy. In certain specific embodiments, $R^2$ is -Me, -Et, or —$CF_3$.

In various embodiments, the 5,5-heteroaromatic compound of a formula described herein is N-(4-(4-chlorophenoxy)benzyl)-2,6-dimethylimidazo[2,1-b]thiazole-5-carboxamide. In other embodiments, the compound is one or more of the compounds illustrated in Table 1 that fall within the scope of a particular recited formula. In some embodiments, a formula, composition, or method excludes any compound disclosed by WO 2008/38251 or U.S. Patent Publication No. 2010/222600. In various embodiments of the formula and compounds described herein, heterocycles are not directly linked together by carbonyl moieties.

The invention thus provides novel compounds of the formulas described herein, intermediates for the synthesis of compounds of the formulas described herein, as well as methods of preparing compounds of the formulas described herein. The invention also provides compounds of the formulas described herein that are useful as intermediates for the synthesis of other useful compounds. The invention provides for the use of compounds of the formulas described herein for the manufacture of medicaments useful for the treatment of bacterial infections in a mammal, such as a human.

The invention further provides for the use of the compounds and compositions described herein for use in killing or inhibiting the growth of bacteria, and for use in medical therapy. The medical therapy can be treating infections, for example, bacterial infections or multidrug resistant bacterial infections. The invention also provides for the use of a composition as described herein for the manufacture of a medicament to treat a disease in a mammal, for example, a bacterial infection in a human. The composition or medicament can include a pharmaceutically acceptable diluent, excipient, or carrier.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

FIG. 1. An X-ray crystal structure determined for N-(4-(4-chlorophenoxy)benzyl)-2,6-dimethylimidazo[2,1-b]thiazole-5-carboxamide (ND-010081).

DETAILED DESCRIPTION

Definitions

As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14th Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrase "one or more" is readily understood by one of skill in the art, particularly when read in context of its usage. For example, one or more substituents on a phenyl ring refers to one to five, or one to four, for example if the phenyl ring is disubstituted.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values, e.g., weight percentages, proximate to the recited range that are equivalent in terms of the functionality of the individual ingredient, the composition, or the embodiment. The term about can also modify the end-points of a recited range as discuss above in this paragraph.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

Various operations may be described as multiple discrete operations in turn, in a manner that may be helpful in understanding embodiments. However, the order of description should not be construed to imply that these operations are order dependent.

The description may use the terms "embodiment" or "embodiments", which may each refer to one or more of the same or different embodiments. Furthermore, the terms "comprising", "including", "having", and the like, as used with respect to embodiments, are synonymous.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to treat a disease, disorder, and/or condition, or to bring about a recited effect. For example, an effective amount can be an amount effective to reduce the progression or severity of the condition or symptoms being treated. Determination of a therapeutically effective amount is well within the capacity of persons skilled in the art, especially in light of the disclosure provided herein. The term "effective amount" is intended to include an amount of a compound described herein, or an amount of a combination of compounds described herein, e.g., that is effective to treat or prevent a disease or disorder, or to treat the symptoms of the disease or disorder, in a host. Thus, an "effective amount" generally means an amount that provides the desired effect.

The terms "treating", "treat" and "treatment" include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" can extend to prophylaxis and can include prevent, prevention, preventing, lowering, stopping or reversing the progression or severity of the condition or symptoms being treated. As such, the term "treatment" can include medical, therapeutic, and/or prophylactic administration, as appropriate.

The terms "inhibit", "inhibiting", and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting.

The term "halogen" or "halo" refers to fluoro, bromo, chloro, or iodo substituents.

The term "alkyl" refers to a cyclic, branched, or straight chain alkyl group containing only carbon and hydrogen, and unless otherwise mentioned contains one to twelve carbon atoms. This term may be further exemplified by groups such as methyl, ethyl, n-propyl, isopropyl, isobutyl, t-butyl, pentyl, pivalyl, heptyl, adamantyl, and cyclopentyl. Alkyl groups can either be unsubstituted or substituted with one or more substituents, for instance, halogen, alkyl, alkoxy, alkylthio, trifluoromethyl, acyloxy, hydroxy, mercapto, carboxy, aryloxy, aryl, arylalkyl, heteroaryl, amino, alkylamino, dialkylamino, morpholino, piperidino, pyrrolidin-1-yl, piperazin-1-yl, or other functionality to form a "substituted alkyl" or "functionalized alkyl".

Thus, an alkyl can be a branched or unbranched hydrocarbon having, for example, from 1-20 carbon atoms, and often 1-12, 1-10, 1-8, 1-6, or 1-4 carbon atoms. Examples include, but are not limited to, methyl, ethyl, 1-propyl, 2-propyl (iso-propyl), 1-butyl, 2-methyl-1-propyl (isobutyl), 2-butyl (sec-butyl), 2-methyl-2-propyl (t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, and the like. The alkyl can be unsubstituted or substituted, for example, with a substituent as described for a compound or formula herein, or a substituent as described below. The alkyl can also be optionally partially or fully unsaturated. As such, the recitation of an alkyl group can include both alkenyl and alkynyl groups. The alkyl can be a monovalent hydrocarbon radical, as described and exemplified above, or it can be a divalent hydrocarbon radical (i.e., an alkylene).

The term "substituted" indicates that one or more hydrogen atoms on the group indicated in the expression using "substituted" is replaced with a "substituent". The number referred to by 'one or more' can be apparent from the moiety on which the substituents reside. For example, one or more can refer to, e.g., 1, 2, 3, 4, 5, or 6; in some embodiments 1, 2, or 3; and in other embodiments 1 or 2, and if the substituent is an oxo group, two hydrogen atoms are replace by the presence of the substituent. The substituent can be one of a selection of indicated groups, or it can be a suitable group recited below or known to those of skill in the art, provided that the substituted atom's normal valency is not exceeded, and that the substitution results in a stable compound. Suitable substituent groups include, e.g., alkyl, alkenyl, alkynyl, alkoxy, halo, haloalkyl, hydroxy, hydroxyalkyl, aryl, aroyl, (aryl)alkyl (e.g., benzyl or phenylethyl), heteroaryl, heterocycle, cycloalkyl, alkanoyl, alkoxycarbonyl, alkylcarbonyloxy, amino, alkylamino, dialkylamino, trifluoromethyl, trifluoromethoxy, trifluoromethylthio, difluoromethyl, acylamino, nitro, carboxy, carboxyalkyl, keto, thioxo, alkylthio, alkylsulfinyl, alkylsulfonyl, arylsulfinyl, arylsulfonyl, heteroarylsulfinyl, heteroarylsulfonyl, heterocyclesulfinyl, heterocyclesulfonyl, phosphate, sulfate, hydroxyl amine, hydroxyl (alkyl)amine, and cyano, as well as the moieties illustrated in the schemes and Figures of this disclosure, and combinations thereof. Additionally, suitable substituent groups can be, e.g., —X, —R, —O$^-$, —OR, —SR, —S$^-$, —NR$_2$, —NR$_3$, =NR, —CX$_3$, —CN, —OCN, —SCN, —N=C=O, —NCS, —NO, —NO$_2$, =N$_2$, —N$_3$, —NC(=O)R, —C(=O)R, —C(=O)NRR, —S(=O)$_2$O$^-$, —S(=O)$_2$OH, —S(=O)$_2$R, —OS(=O)$_2$OR, —S(=O)$_2$NR, —S(=O)R, —OP(=O)(OR)$_2$, —P(=O)(OR)$_2$, —OP(=O)(OH)(OR), —P(=O)(OH)(OR), —P(=O)(O$^-$)$_2$, —P(=O)(OH)$_2$, —C(=O)R, —C(=O)X, —C(S)R, —C(O)OR, —C(O)O$^-$, —C(S)OR, —C(O)SR, —C(S)SR, —C(O)NRR, —C(S)NRR, or —C(NR)NRR, where each X is independently a halogen ("halo"): F, Cl, Br, or I; and each R is independently H, alkyl, aryl, (aryl)alkyl (e.g., benzyl), heteroaryl, (heteroaryl)alkyl, heterocycle, heterocycle(alkyl), or a protecting group. As would be readily understood by one skilled in the art, when a substituent is keto (=O) or thioxo (=S), or the like, then two hydrogen atoms on the substituted atom are replaced. In some embodiments, one or more of the substituents above can be excluded from the group of potential values for substituents on the substituted group. The various R groups in the schemes and figures of this disclosure can be one or more of the substituents recited above, thus the listing of certain variables for such R groups (including R$^1$, R$^2$, R$^3$, etc.) are representative and not exhaustive, and can be supplemented with one or more of the substituents above.

Alkyl chains can be optionally interrupted, for example, with one or more heteroatoms. The term "interrupted" indicates that another group is inserted between two adjacent carbon atoms, and the hydrogen atoms to which they are attached (e.g., methyl (CH$_3$), methylene (CH$_2$) or methine (CH)), of a particular carbon chain being referred to in the expression using the term "interrupted", provided that each of the indicated atom's normal valency is not exceeded, and that the interruption results in a stable compound. Suitable groups that can interrupt a carbon chain include, e.g., with one or more non-peroxide oxy (—O—), thio (—S—), imino (—N(H)—), methylenedioxy (—OCH$_2$O—), carbonyl (—C(=O)—), carboxy (—C(=O)O—), carbonyldioxy (—OC(=O)O—), carboxylato (—OC(=O)—), imine (C=NH), sulfinyl (SO) and sulfonyl (SO$_2$). Alkyl groups can be interrupted by one or more (e.g., 1, 2, 3, 4, 5, or about 6) of the aforementioned suitable groups. The site of interruption can also be between a carbon atom of an alkyl group and a carbon atom to which the alkyl group is attached. An alkyl group that is interrupted by a heteroatom therefor forms a heteroalkyl group.

When an alkyl group can be substituted, it can thus be a "substituted allyl". The term "substituted alkyl" refers to an alkyl moiety that can include 1-4 substituents selected from halogen, het, cycloalkyl, cycloalkenyl, aryl, amino, cyano, nitro, —OQ$_{10}$, —SQ$_{10}$, —S(O)$_2$Q$_{10}$, —S(O)Q10, —OS(O)$_2$Q$_{10}$, —C(=NQ$_{10}$)Q$_{10}$, —C(=NOQ$_{10}$)Q$_{10}$, —S(O)$_2$—N=S(O)(Q$_{10}$)$_2$, —S(O)$_2$—N=S(Q$_{10}$)$_2$, —NQ$_{10}$Q$_{10}$, —C(O)Q$_{10}$, —C(S)Q$_{10}$, —C(O)OQ$_{10}$, —OC(O)Q$_{10}$, —C(O)NQ$_{10}$Q$_{10}$, —C(S)NQ$_{10}$Q$_{10}$, —N(Q$_{10}$)C(S)NQ$_{10}$Q$_{10}$, —C(O)NQ$_{10}$Q$_{10}$, —C(S)NQ$_{10}$Q$_{10}$, —C(O)C(Q$_{16}$)$_2$OC(O)Q$_{10}$, —CN, =S, —NQ$_{10}$C(O)Q$_{10}$, —NQ$_{10}$C(O)NQ$_{10}$Q$_{10}$, —S(O)$_2$NQ$_{10}$Q$_{10}$, —NQ$_{10}$S(O)$_2$Q$_{10}$, —NQ$_{10}$S(O)Q$_{10}$, —NQ$_{10}$SQ$_{10}$, and —SNQ$_{10}$Q$_{10}$. Each of the het, cycloalkyl, cycloalkenyl, and aryl can be optionally substituted with 1-4 substituents independently selected from halogen and Q$_{15}$.

The term "cycloalkyl" refers to a cyclic alkyl moiety. Unless otherwise stated, cycloalkyl moieties include about 3 to about 8, 9, or 10 carbon atoms. Thus, the term "cycloalkyl" refers to cyclic alkyl groups of, for example, from 3 to 10 carbon atoms having a single cyclic ring or multiple condensed rings. Cycloalkyl groups include, by way of example, single ring structures such as cyclopropyl, cyclobutyl, cyclopentyl, cyclooctyl, and the like, or multiple ring structures such as adamantyl, and the like. The cycloalkyl can be unsubstituted or substituted. The cycloalkyl group can be monovalent or divalent (e.g., linking two groups together), and can be optionally substituted as described for alkyl groups. The cycloalkyl group can optionally include one or more cites of unsaturation, for example, the cycloalkyl group can include one or more carbon-carbon double bonds, such as, for example, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and the like.

The term "alkene" refers to a hydrocarbon molecule with the general formula C$_n$H$_{2n}$ that contains one or more double bonds.

The term "alkyne" refers to a moiety having the general formula C$_2$H$_{2n-2}$ corresponding to carbon chains with a triple carbon-carbon bond included.

The term "alkoxy" refers to the group —O-alkyl, where alkyl is as defined herein. Examples of alkoxy groups include, but are not limited to, methoxy, ethoxy, n-propoxy, iso-propoxy, n-butoxy, tert-butoxy, sec-butoxy, n-pentoxy, n-hexoxy, 1,2-dimethylbutoxy, and the like. The alkoxy can be unsubstituted or substituted.

The term "alcohol" refers to any organic compound in which a hydroxyl group (—OH) is bound to a carbon atom of an alkyl or substituted alkyl group. The general formula for simple acyclic alcohols is $C_nH_{2n+1}OH$.

The term "epoxide" refers to any of a class of organic compound, cyclic ethers, having a three-member ring.

The term "ketone" refers to an organic compound containing the carbonyl group, >C=O, to which other carbon atoms are attached.

The term "ester" refers to the product of the reaction between a carboxylic acid and an alcohol.

The term "ether" refers to an organic compound containing the functional group RO—R' where R and R' are the organic groups such as alkyl or aryl.

The term "aldehyde" refers to an organic compound containing a —CHO group.

The term "nitrile" refers to any of a class of organic compounds containing the cyano radical —CN.

The term "thiol" refers to a molecular group that includes a bonded sulfur and hydrogen atom (—SH).

The term "thioester" refers to a compound resulting from the bonding of sulfur with an acyl group with the general formula R—S—CO—R'. Thioesters are the product of esterification between a carboxylic acid and a thiol (as opposed to an alcohol in regular esters).

The term "sulfide" refers to an organic compound containing sulfur bonded to carbon. The term "disulfide" refers to the structural unit composed of a linked pair of sulfur atoms.

The term "sulfone" refers to a chemical compound containing a sulfonyl functional group attached to two carbon atoms. The central sulfur atom is twice double bonded to oxygen and has two further hydrocarbon substituents. The general structural formula is R—S(=O)$_2$R' where R and R' are the organic groups such as alkyl or aryl, or a portion of a formula described herein. For example, a methylsulfone group is a —S(=O)$_2$Me group.

The term "sulfoxide" refers to a chemical compound containing a sulfonyl functional group attached to two carbon atoms. Sulfoxides can be considered oxidized sulfides.

The term "amine" refers to NH$_2$, NHR, or NR$_2$. Unless otherwise stated R can be alkyl, alkenyl, alkynyl, cycloalkyl, cycloalkenyl, het or aryl.

The term "amide" refers to an organic compound containing the —CONH— group.

The term "urea" refers to an organic compound with the chemical formula (NH$_2$)$_2$CO or RNHCONHR' where R and R' are the organic groups such as alkyl or aryl, or a portion of a formula described herein.

The term "carbamate" refers to any of a group of organic compounds sharing a common functional group with the general structure —NH(CO)O—. Carbamates are esters of carbamic acid, NH$_2$COOH. Since carbamic acid contains nitrogen attached to a carboxyl group, it is also an amide. Therefore, carbamate esters may have alkyl or aryl groups substituted on the nitrogen, or the amide function. For example, ethyl carbamate is unsubstituted, whereas ethyl N-methylcarbamate has a methyl group attached to the nitrogen.

The term "aryl" refers to an aromatic hydrocarbon group derived from the removal of at least one hydrogen atom from a single carbon atom of a parent aromatic ring system. The radical attachment site can be at a saturated or unsaturated carbon atom of the parent ring system. The aryl group can have from 6 to 30 carbon atoms, for example, about 6-10 carbon atoms. The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or optionally substituted, as described for alkyl groups. Thus, the term "aryl" can refer to phenyl, substituted phenyl, naphthyl, and substituted naphthyl.

The term "heterocycle" refers to a saturated or partially unsaturated ring system, containing at least one heteroatom selected from the group oxygen, nitrogen, silicon, and sulfur, and optionally substituted with one or more groups as defined for the term "substituted". A heterocycle can be a monocyclic, bicyclic, or tricyclic group. A heterocycle group also can contain an oxo group (=O) or a thioxo (=S) group attached to the ring. Non-limiting examples of heterocycle groups include 1,3-dihydrobenzofuran, 1,3-dioxolane, 1,4-dioxane, 1,4-dithiane, 2H-pyran, 2-pyrazoline, 4H-pyran, chromanyl, imidazolidinyl, imidazolinyl, indolinyl, isochromanyl, isoindolinyl, morpholinyl, piperazinyl, piperidinyl, pyrazolidinyl, pyrazolinyl, pyrrolidine, pyrroline, quinuclidine, tetrahydrofuranyl, and thiomorpholine.

By way of example and not limitation, carbon bonded heterocycles can be bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, 5-thiazolyl, and the like. Various combinations of the aforementioned positions are included in the compounds described herein.

By way of example and not limitation, nitrogen bonded heterocycles can be bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. In one embodiment, nitrogen bonded heterocycles include 1-aziridyl, 1-azetedyl, 1-pyrrolyl, 1-imidazolyl, 1-pyrazolyl, and 1-piperidinyl.

Further examples of "heterocycles" include but are not limited to pyridine, thiophene, furan, pyrazoline, pyrimidine, 2-pyridyl, 3-pyridyl, 4-pyridyl, 2-pyrimidinyl, 4-pyrimidinyl, 5-pyrimidinyl, 3-pyrazinyl, 3-pyridazinyl, 4-pyridazinyl, 4-oxo-2-imidazolyl, 1,2,4-oxadiazole, 1,3,4-oxadiazole, 4-pyridazinyl, 3-pyrazinyl, 4-oxo-2-imidazolyl, 2-imidazolyl, 4-imidazolyl, 3-isoxazolyl, 4-isoxazolyl, 5-isoxazolyl, 3-pyrazolyl, 4-pyrazolyl, 5-pyrazolyl, 2-oxazolyl, 4-oxazolyl, 4-oxo-2-oxazolyl, 5-oxazolyl, 1,2,3-oxathiazole, 1,2,3-oxadiazole, 1,2,5-oxadiazole, 2-thiazolyl, 5-thiazolyl, 3-isothiazole, 4-isothiazole, 5-isothiazole, 2-furanyl, 3-furanyl, 2-thienyl, 3-thienyl, 2-pyrrolyl, 3-pyrrolyl, 3-isopyrrolyl, 4-isopyrrolyl, 5-isopyrrolyl, 1,2,3-oxathiazole-1-oxide, 1,2,4-oxadiazol-3-yl, 1,2,4-oxadiazol-5-yl, 5-oxo-1,2,4-oxadiazol-3-yl, 1,2,4-thiadiazol-3-yl, 1,2,4-thiadiazol-5-yl, 3-oxo-1,2,4-thiadiazol-5-yl, 1,3,4- thiadiazol-5-yl, 2-oxo-1,3,4-thiadiazol-5-yl, 1,2,4-triazol-3-yl, 1,2,4-triazol-5-yl, 1,2,3,4-tetrazol-5-yl, 5-oxazolyl, 3-isothiazolyl, 4-isothiazolyl, 5-isothiazolyl, 1,3,4-oxadiazole, 4-oxo-2-thiazolinyl, 5-methyl-1,3,4-thiadiazol-2-yl, thiazoledione, 1,2,3,4-thiatriazole, 1,2,4-dithiazolone, phthalimide, quinolinyl, morpholinyl, benzimidazolyl, benzo[d]thiazolyl, benzo[d]oxazolyl, diazinyl, triazinyl, quinolinyl, quinoxalinyl, naphthyridinyl, azetidinyl, pyrrolidinyl, hydantoinyl, oxathiolanyl, dioxolanyl, imidazolidinyl, azabicyclo[2.2.1]heptyl, 2-methyl-1,4-dioxa-8-azaspiro[4.5]decane, 2,3-dimethyl-1,4-dioxa-8-azaspiro[4.5]decane, 3-methyl-1,5-dioxa-9-azaspiro[5.5]undecane, and 2,4-dimethyl-1,5-dioxa-9-azaspiro[5.5]undecane.

The terms "heterocyclic," "heterocycle," and "het" are used interchangeably and thus refer to organic compounds containing at least one atom of carbon, and at least one element other than carbon, such as sulfur, oxygen or nitrogen within a ring structure. These structures may comprise either simple aromatic rings or non-aromatic rings. Each monocyclic ring may be aromatic, saturated or partially unsaturated. A bicyclic ring system may include a monocyclic ring containing one or more heteroatom fused with a cycloalkyl or aryl group. A bicyclic ring system may also include a monocyclic ring containing one or more heteroatom fused with another monocyclic ring system.

The term "heteroaryl" refers to a monocyclic, bicyclic, or tricyclic ring system containing one, two, or three aromatic rings and containing at least one nitrogen, oxygen, or sulfur atom in an aromatic ring. The heteroaryl can be unsubstituted or substituted, for example, with one or more, and in particular one to three, substituents, as described in the definition of "substituted". Typical heteroaryl groups contain 2-20 carbon atoms in the ring skeleton in addition to the one or more heteroatoms. Examples of heteroaryl groups include, but are not limited to, 2H-pyrrolyl, 3H-indolyl, 4H-quinolizinyl, acridinyl, benzo[b]thienyl, benzothiazolyl, β-carbolinyl, carbazolyl, chromenyl, cinnolinyl, dibenzo[b,d]furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrrolyl, quinazolinyl, quinolyl, quinoxalinyl, thiadiazolyl, thianthrenyl, thiazolyl, thienyl, triazolyl, tetrazolyl, and xanthenyl. In one embodiment the term "heteroaryl" denotes a monocyclic aromatic ring containing five or six ring atoms containing carbon and 1, 2, 3, or 4 heteroatoms independently selected from non-peroxide oxygen, sulfur, and N(Z) wherein Z is absent or is H, O, alkyl, aryl, or $(C_1-C_6)$alkylaryl. In some embodiments, heteroaryl denotes an ortho-fused bicyclic heterocycle of about eight to ten ring atoms derived therefrom, particularly a benz-derivative or one derived by fusing a propylene, trimethylene, tetramethylene, or 1,2-methylenedixoy diradical thereto.

The term "heteroaryl" can thus refer to a mono- or bicyclic het in which one or more cyclic ring is aromatic. The term "substituted heteroaryl" refers to a heteroaryl moiety substituted with one or more functional groups selected from halogen, alkyl, hydroxyl, amino, alkoxy, cyano, and nitro, or another substituent as described herein.

The term "morpholine" refers to the cyclic organic compound or moiety having the chemical formula $O(CH_2CH_2)_2NH$. This heterocycle features both amine and ether functional groups. Because of the amine, morpholine is a base; its conjugate acid is called morpholinium. For example, when morpholine is neutralized by hydrochloric acid, one obtains the salt morpholinium chloride. Morpholine can be a substituent of organic groups such as alkyl and aryl.

The term "thiomorpholine" refers to $C_4H_9NS$, and is a heterocyclic compound containing nitrogen and sulfur. It may be considered a thio derivative of morpholine.

The term "piperazine" refers to an organic compound that consists of a six-member ring containing two opposing nitrogen atoms.

The term "piperidine" refers to an organic compound with the molecular formula $(CH_2)_5NH$. This heterocyclic amine consists of a six-member ring containing five methylene units and one nitrogen atom.

The term "acyl" refers to any of a group or radical of the form RCO— where R is an organic group such as alkyl or aryl.

The term "furan" refers to any of a class of aromatic heterocyclic compounds containing a ring of four carbon atoms and an oxygen atom; for instance, $C_4H_4O$. The term "nitrofuran" refers to a furan ring with a nitro group substituent.

The term "thiophene" refers to a heterocyclic compound with the formula $C_4H_4S$. Consisting of a flat five-membered ring, it is aromatic as indicated by its extensive substitution reactions. Related to thiophene are benzothiophene and dibenzothiophene, containing the thiophene ring fused with one and two benzene rings, respectively. The term "nitrothiophene" refers to a thiophene ring with a nitro group substituent. Compounds analogous to thiophene include furan ($C_4H_4O$) and pyrrole ($C_4H_4NH$).

The term "imidazole" refers to an organic compound with the formula $C_3H_4N_2$. This aromatic heterocycle is classified as an alkaloid. Imidazole refers to the parent compound whereas imidazoles are a class of heterocycles with similar ring structure but varying substituents. A nitroimidazole is an imidazole derivative that contains a nitro group.

The term "oxazole" refers to a five-member heterocycle having three carbon atoms, one oxygen atom, one nitrogen atom and two double bonds; the 1,3-isomer is aromatic.

The tem "oxazoline" refers to an unsaturated heterocyclic compound containing a five-member ring, two double bonds, one nitrogen and one oxygen atom; and any derivative of this compound.

The term "thiazole" refers to any of a class of unsaturated heterocyclic compounds containing a ring of three carbon atoms, a sulfur and an nitrogen atom; for instance the simplest one, $C_3H_3SN$.

The term "thiazoline" refers to an unsaturated heterocyclic compound containing a five-member ring, two double bonds, one nitrogen and one sulfur atom; and any derivative of this compound.

The term "triazole" refers to either one of a pair of isomeric chemical compounds with molecular formula $C_2H_3N_3$, having a five-member ring of two carbon atoms and three nitrogen atoms.

The term "pyridine" refers to any of a class of aromatic heterocyclic compounds containing a ring of five carbon atoms and a nitrogen atom; for instance the simplest one, $C_5H_5N$.

The term "pyrazine" refers to a diazine in which the two nitrogen atoms are in the para-position.

The term "naphthalene" refers to an aromatic, white, solid hydrocarbon with formula $C_{10}H_8$ and the structure of two fused benzene rings.

The term "diketopiperazine" refers to a class of cyclic organic compounds that result from peptide bonds between two amino acids to form a lactam. They are the smallest possible cyclic peptides.

The term "quinoline" refers to any of a class of aromatic heterocyclic compounds containing a benzene ring fused with a ring of five carbon atoms and a nitrogen atom; for instance the simplest one, $C_9H_7N$. Isoquinoline, also known as benzo[c]pyridine or 2-benzanine, is a heterocyclic aromatic organic compound. It is a structural isomer of quinoline. Isoquinoline and quinoline are benzopyridines, which are composed of a benzene ring fused to a pyridine ring. In a broader sense, the term isoquinoline is used to make reference to isoquinoline derivatives.

The term "oxazolidinone" refers to a class of heterocyclic organic compounds containing both nitrogen and oxygen in a 5-member ring.

The term "substituted aryl" can thus refer to an aryl moiety having 1-3 substituents selected from halogen, het, alkyl, substituted alkyl, alkenyl, alkynyl, alkoxy, cycloalkyl, cycloalkenyl, aryl, cyano, nitro, —$OQ_{10}$, —$SQ_{10}$, —$S(O)_2Q_{10}$, —$S(O)Q_{10}$, —$OS(O)_2Q_{10}$, —$C(=NQ_{10})Q_{10}$, —$C(=NOQ_{10})Q_{10}$, —$S(O)_2$—$N=S(O)(Q_{10})_2$, —$S(O)_2$—$N=S(Q_{10})_2$, —$NQ_{10}Q_{10}$, —$C(O)Q_{10}$, —$C(S)Q_{10}$, —$C(O)OQ_{10}$, —$OC(O)Q_{10}$, —$C(O)NQ_{10}Q_{10}$, —$C(S)NQ_{10}Q_{10}$, —$C(O)C(Q_{16})_2OC(O)Q_{10}$, —$NQ_{10}C(O)Q_{10}$, —$N(Q_{10})C(S)NQ_{10}Q_{10}$, —$N(Q_{10})C(S)Q_{10}$, —$NQ_{10}C(O)NQ_{10}Q_{10}$, —$S(O)_2NQ_{10}Q_{10}$, —$NQ_{10}S(O)_2Q_{10}$, —$NQ_{10}S(O)Q_{10}$, —$NQ_{10}SQ_{10}$, and —$SNQ_{10}Q_{10}$. The het, cycloalkyl, cycloalkenyl, alkenyl, alkynyl, and aryl being optionally substituted with 1-3 substituents selected from halogen and $Q_{15}$.

Each $Q_{10}$ is independently selected from H, alkyl, cycloalkyl, het, cycloalkenyl, and aryl. The het, cycloalkyl, cycloalkenyl, and aryl being optionally substituted with 1-3 substituents selected from halo and $Q_{13}$.

Each $Q_{11}$ is independently selected from H, halogen, alkyl, aryl, cycloalkyl, and het. The alkyl, aryl, cycloalkyl, and het being optionally substituted with 1-3 substituents independently selected from halogen, nitro, cyano, $=S$, $=O$, and $Q_{14}$.

Each $Q_{13}$ is independently selected from $Q_{11}$, —$OQ_{11}$, —$SQ_{11}$, —$S(O)_2Q_{11}$, —$S(O)Q_{11}$, —$OS(O)_2Q_{11}$, —$C(=NQ_{11})Q_{11}$, —$S(O)_2$—$N=S(O)(Q_{11})_2$, —$S(O)_2$—$N=S(Q_{11})_2$, —$SC(O)Q_{11}$, —$NQ_{11}Q_{11}$, —$C(O)Q_{11}$, —$C(S)Q_{11}$, —$C(O)OQ_{11}$, —$OC(O)Q_{11}$, —$C(O)NQ_{11}Q_{11}$, —$(S)NQ_{11}Q_{11}$, —$C(O)C(Q_{16})_2OC(O)Q_{10}$, —$CN$, $=O$, $=S$, —$NQ_{11}C(O)Q_{11}$, —$NQ_{11}C(S)Q_{11}$, —$NQ_{11}C(O)NQ_{11}Q_{11}$, —$NQ_{11}C(S)NQ_{11}Q_{11}$, —$S(Q)_2NQ_{11}Q_{11}$, —$NQ_{11}S(O)_2Q_{11}$, —$NQ_{11}S(O)Q_{11}$, —$NQ_{11}SQ_{11}$, —$NO_2$, and —$SNQ_{11}Q_{11}$.

Each $Q_{14}$ is independently selected from H, alkyl, cycloalkyl, phenyl, or naphthyl, each optionally substituted with 1-4 substituents independently selected from F, Cl, Br, I, —$OQ_{16}$, —$SQ_{16}$, —$S(O)_2Q_{16}$, —$S(O)Q_{16}$, —$OS(O)_2Q_{16}$, —$NQ_{16}Q_{16}$, —$C(O)Q_{16}$, —$C(S)Q_{16}$, —$C(O)OQ_{16}$, —$NO_2$, —$C(O)NQ_{16}Q_{16}$, —$C(S)NQ_{16}Q_{16}$, —$CN$, —$NQ_{16}C(O)Q_{16}$, —$NQ_{16}C(S)Q_{16}$, —$NQ_{16}C(O)NQ_{16}Q_{16}$, —$NQ_{16}C(S)NQ_{16}Q_{16}$, —$S(O)_2NQ_{16}Q_{16}$, and —$NQ_{16}S(O)_2Q_{16}$. The alkyl, cycloalkyl, and cycloalkenyl being further optionally substituted with $=O$ or $=S$.

Each $Q_{15}$ is independently selected from H, alkyl, cycloalkyl, heteroaryl, phenyl, or naphthyl, each optionally substituted with 1-4 substituents independently selected from F, Cl, Br, I, —$OQ_{16}$, —$SQ_{16}$, —$S(O)_2Q_{16}$, —$S(O)Q_{16}$, —$OS(O)_2Q_{16}$, —$C(=NQ_{16})Q_{16}$, —$S(O)_2$—$N=S(O)(Q_{16})_2$, —$S(O)_2$—$N=S(Q_{16})_2$, —$SC(O)Q_{16}$, —$NQ_{16}Q_{16}$, —$C(O)Q_{16}$, —$C(S)Q_{16}$, —$C(O)OQ_{16}$, —$OC(O)Q_{16}$, —$C(S)NQ_{16}Q_{16}$, —$C(O)C(Q_{16})_2OC(O)Q_{16}$, —$CN$, —$NQ_{16}C(O)Q_{16}$, —$NQ_{16}C(S)Q_{16}$, —$NQ_{16}C(O)NQ_{16}Q_{16}$, —$NQ_{16}C(S)NQ_{16}Q_{16}$, —$S(O)_2NQ_{16}Q_{16}$, —$NQ_{16}S(O)_2Q_{16}$, —$NQ_{16}S(O)Q_{16}$, —$NQ_{16}SQ_{16}$, —$NO_2$, and —$SNQ_{16}Q_{16}$. The alkyl, cycloalkyl, and cycloalkenyl can be further optionally substituted with $=O$ or $=S$.

Each $Q_{16}$ is independently selected from H, alkyl, and cycloalkyl. The alkyl and cycloalkyl optionally including 1-3 halogens.

Various embodiments of the disclosure provide novel heteroaromatic compounds, for instance 5,5-heteroaromatics. Some embodiments are directed to compounds and methods for the treatment and prevention of mycobacterial infections, such as those caused by *M. tuberculosis* and *M. avium*. Other embodiments provide for the synthesis of the disclosed 5,5-heteroaromatic compounds.

In various embodiments, the 5,5-heteroaromatic compounds of this disclosure may be useful in treating or preventing a mycobacterial infection in a subject. The in vitro activity of disclosed compounds may be assessed by standard testing procedures, for instance in $H_{37}Rv$ TB screens.

In some embodiments, the 5,5-heteroaromatic compounds described herein may be useful for treating (for instance, ameliorating or preventing) a *M. tuberculosis* infection, such as multi-drug resistant (MDR) TB or non-MDR TB, and/or a *M. avium* infection in a subject. A compound may be administered to a subject locally or systemically. In various embodiments, a 5,5-heteroaromatic compound may be administered parenterally, for instance subcutaneously, intravenously, or intramuscularly, or it may be administered orally or by inhalation. In various embodiments, such a 5,5-heteroaromatic compound may be used alone or in combination with other anti-mycobacterial agents. In some embodiments, a 5,5-heteroaromatic compound may be administered in varying concentrations depending upon the infection's susceptibility to the compound being administered, the extent of the disease, whether the infection is latent or active, whether the infection is drug-resistant, and the general health of the subject.

In various embodiments, one or more 5,5-heteroaromatic compounds may be incorporated into a pharmaceutical composition. Embodiments of the present disclosure encompass any racemic, optically-active, polymorphic, tautomeric, or stereoisomeric form or mixture thereof, of a compound of the disclosure, which possesses the useful properties described herein.

In cases where compounds are sufficiently basic or acidic to form stable nontoxic acid or base salts, use of the compounds as pharmaceutically acceptable salts may be appropriate. Examples of pharmaceutically acceptable salts within the scope of embodiments herein include organic acid addition salts formed with acids that form a physiologically acceptable anion and inorganic salts.

Pharmaceutical compositions in accordance with embodiments of the disclosure may be prepared by combining the disclosed compounds with a solid or liquid pharmaceutically acceptable carrier and, optionally, with pharmaceutically acceptable adjuvants and excipients employing standard and conventional techniques. Solid form compositions include powders, tablets, dispersible granules, capsules, cachets and suppositories. A solid carrier may be at least one substance that may also function as a diluent, flavoring agent, solubilizer, lubricant, suspending agent, binder, tablet disintegrating agent, and encapsulating agent. Inert solid carriers include magnesium carbonate, magnesium stearate, talc, sugar, lactose, pectin, dextrin, starch, gelatin, cellulosic materials, low melting wax, cocoa butter, and the like. Liquid form compositions include solutions, suspensions and emulsions. For example, there may be provided solutions of the compounds disclosed herein dissolved in water and water-propylene glycol systems, optionally containing suitable conventional coloring agents, flavoring agents, stabilizers, and/or thickening agents.

In some embodiments, a pharmaceutical composition may be provided employing conventional techniques in unit dosage form containing effective or appropriate amounts of one or more active component. In various embodiments, the quantity of active component (compound) in a pharmaceutical composition and unit dosage form thereof may be varied or adjusted widely depending upon the particular application, the potency of the particular compound and the desired concentration. In an exemplary embodiment, the quantity of active component may range from 0.5% to 90% by weight of the composition.

In various embodiments, in therapeutic uses for treating, ameliorating, preventing, or combating a mycobacterial infection in a subject, such as an infection caused by *M. tuberculosis* or *M. avium*, the compounds or pharmaceutical compositions thereof may be administered orally, parenterally, and/or by inhalation at a dosage to obtain and maintain a concentration or blood-level of active component in the animal undergoing treatment that is therapeutically effective. In an embodiment, such a therapeutically effective amount/dosage of active component may be in the range of about 0.1 to about 300 mg/kg, or about 0.1 to about 100 mg/kg, for instance, about 0.1 to about 50 mg/kg, or about 0.1 to about 10 mg/kg, of body weight/day. It is to be understood that the dosages may vary depending upon the requirements of the patient, the severity of the infection, the particular mycobacterial species, whether the infection is latent or active, the drug resistance of the strain, the duration of the infection being treated, and the particular compound being used. Also, it is to be understood that the initial dosage administered may be increased beyond the above upper level in order to rapidly achieve the desired blood-level or the initial dosage may be smaller than the optimum and the daily dosage may be progressively increased during the course of treatment depending on the particular situation. If desired, the daily dose also may be divided into multiple doses for administration, for instance, two to four times per day.

In an embodiment, an initial 5,5-heteroaromatic compound was provided and tested as an exemplary member of the new 5,5-heteroaromatic class of anti-mycobacterial agents disclosed herein. This initial compound is identified below as compound ND-010081, and the compounds structure is shown below in Table 1, along with a series of other exemplary 5,5-heteroaromatic compounds. The 5,5-heteroaromatic class of molecules is unrepresented within the TB and *M. avium* literature, and the scaffold is very attractive because of the low cost of starting materials and the ease with which potent (<1 µg/mL) anti-mycobacterial compounds are synthesized therefrom.

TABLE 1

5,5-heteroaromatic compounds.

| Compound ID | Structure | M.W. |
|---|---|---|
| ND-010081 | 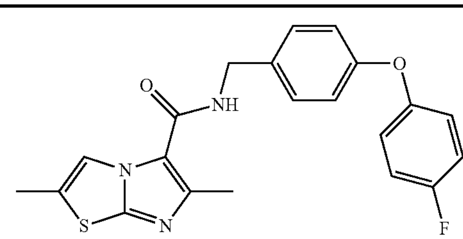 | 395.45 |
| ND-010050 | 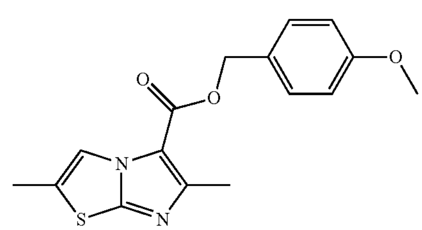 | 316.37 |
| ND-009763 | 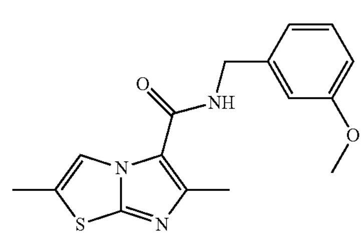 [SMILES: COc1cccc(CNC(=O)c2c(C)nc3sc(C)cn23)c1] | 315.39 |

TABLE 1-continued

| 5,5-heteroaromatic compounds. | | |
|---|---|---|
| Compound ID | Structure | M.W. |
| ND-009762 | 2,6-dimethyl-imidazo[2,1-b]thiazole-5-carboxylic acid (3-fluoro-benzyl)-amide | 303.35 |
| ND-009749 | 2,6-dimethyl-imidazo[2,1-b]thiazole-5-carboxylic acid benzylamide | 285.36 |
| ND-009745 | 6-ethyl-2-methyl-imidazo[2,1-b]thiazole-5-carboxylic acid | 210.25 |
| ND-009744 | 2,3,6-trimethyl-imidazo[2,1-b]thiazole-5-carboxylic acid methyl ester | 224.28 |
| ND-009743 | 6-ethyl-2-methyl-imidazo[2,1-b]thiazole-5-carboxylic acid methyl ester | 224.28 |
| ND-010475 | 2,6-dimethyl-imidazo[2,1-b][1,3,4]thiadiazole-5-carboxylic acid benzyl ester | 287.34 |
| ND-020000 | 2,6-dimethyl-imidazo[2,1-b]thiazole-5-carboxylic acid (3-chloro-benzyl)-amide | 319.18 |

TABLE 1-continued 5,5-heteroaromatic compounds.

| Compound ID | Structure | M.W. |
|---|---|---|
| ND-020000 | 4-Cl benzyl amide of 2,6-dimethylimidazo[2,1-b]thiazole-5-carboxamide | 319.18 |
| ND-020001 | 2-Cl benzyl amide of 2,6-dimethylimidazo[2,1-b]thiazole-5-carboxamide | 319.81 |
| ND-020002 | 2,5-diF benzyl amide of 2,6-dimethylimidazo[2,1-b]thiazole-5-carboxamide | 321.35 |
| ND-020003 | 4-F benzyl amide of 2,6-dimethylimidazo[2,1-b]thiazole-5-carboxamide | 303.35 |
| ND-020004 | 3,5-diF benzyl amide of 2,6-dimethylimidazo[2,1-b]thiazole-5-carboxamide | 321.35 |
| ND-020005 | 3,5-diCl benzyl amide of 2,6-dimethylimidazo[2,1-b]thiazole-5-carboxamide | 354.25 |

TABLE 1-continued 5,5-heteroaromatic compounds.

| Compound ID | Structure | M.W. |
|---|---|---|
| ND-020006 | 2,6-dimethyl-imidazo[2,1-b]thiazole-5-carboxylic acid (4-trifluoromethoxy-benzyl)-amide | 369.36 |
| ND-020007 | 2,6-dimethyl-imidazo[2,1-b]thiazole-5-carboxylic acid (3-trifluoromethoxy-benzyl)-amide | 369.36 |
| ND-020008 | 2,6-dimethyl-imidazo[2,1-b]thiazole-5-carboxylic acid (3-trifluoromethyl-benzyl)-amide | 353.36 |
| ND-020009 | 2,6-dimethyl-imidazo[2,1-b]thiazole-5-carboxylic acid (4-trifluoromethyl-benzyl)-amide | 353.36 |
| ND-020010 | 6-ethyl-2-methyl-imidazo[2,1-b]thiazole-5-carboxylic acid (4-trifluoromethyl-benzyl)-amide | 367.39 |
| ND-020011 | 2-chloro-6-ethyl-imidazo[2,1-b]thiazole-5-carboxylic acid (4-trifluoromethyl-benzyl)-amide | 387.81 |
| ND-020012 | 2-chloro-6-methyl-imidazo[2,1-b]thiazole-5-carboxylic acid (4-trifluoromethyl-benzyl)-amide | 373.78 |

TABLE 1-continued
5,5-heteroaromatic compounds.
| Compound ID | Structure | M.W. |
|---|---|---|
| ND-020013 | 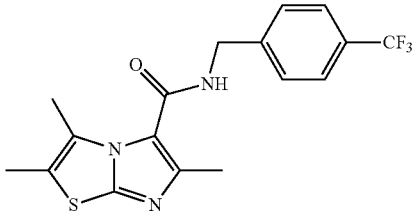 [SMILES: Cc1nc2sc(C)c(C)n2c1C(=O)NCc1ccc(C(F)(F)F)cc1] | 367.39 |
| ND-020014 | 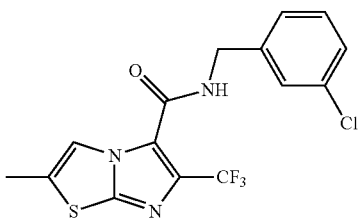 [SMILES: Cc1cn2c(C(=O)NCc3cccc(Cl)c3)c(C(F)(F)F)nc2s1] | 373.78 |
| ND-020015 | 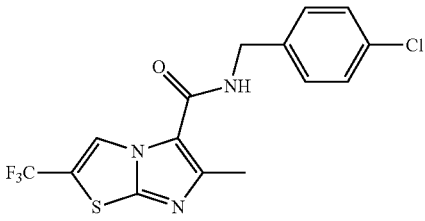 [SMILES: Cc1nc2sc(C(F)(F)F)cn2c1C(=O)NCc1ccc(Cl)cc1] | 373.78 |
| ND-020016 | 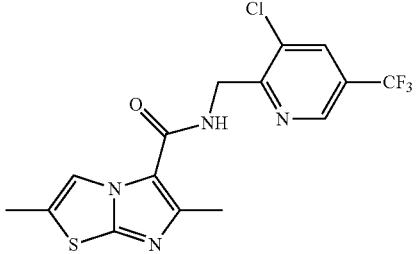 [SMILES: Cc1cn2c(C(=O)NCc3ncc(C(F)(F)F)cc3Cl)c(C)nc2s1] | 388.80 |
| ND-020017 | 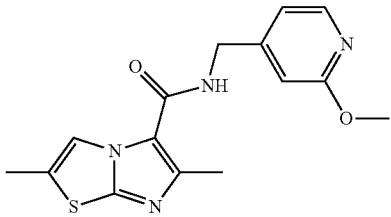 | 316.38 |
| ND-020018 | 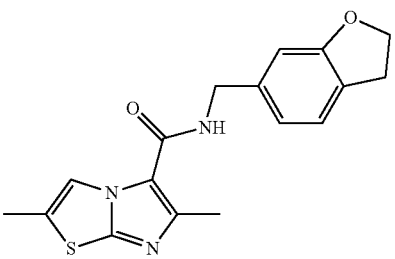 [SMILES: Cc1cn2c(C(=O)NCc3ccc4c(c3)OCC4)c(C)nc2s1] | 327.40 |

TABLE 1-continued 5,5-heteroaromatic compounds.

| Compound ID | Structure | M.W. |
| --- | --- | --- |
| ND-020019 | 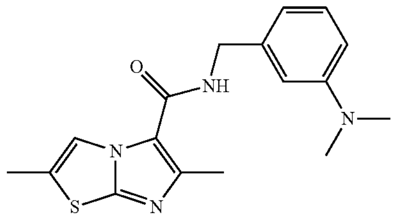 | 238.43 |
| ND-020020 | 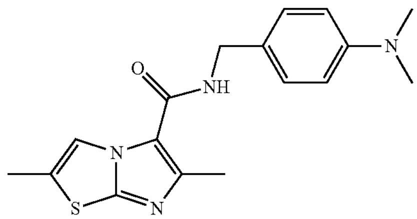 | 238.43 |
| ND-020021 | 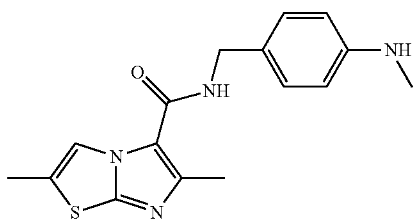 | 314.21 |
| ND-020022 | 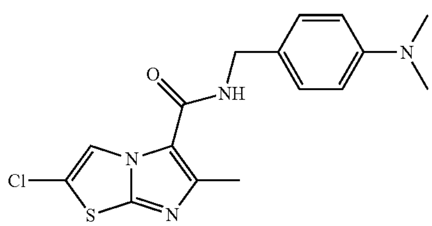 [SMILES: Cc1nc2sc(Cl)cn2c1C(=O)NCc1ccc(N(C)C)cc1] | 248.85 |
| ND-020023 | 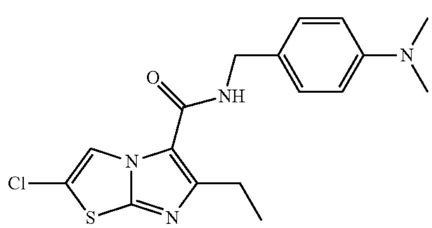 [SMILES: CCc1nc2sc(Cl)cn2c1C(=O)NCc1ccc(N(C)C)cc1] | 362.88 |
| ND-020024 | 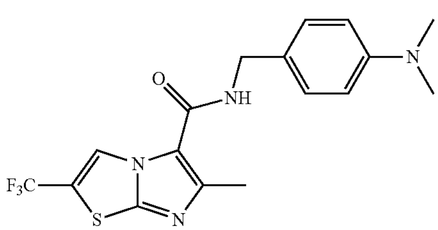 [SMILES: Cc1nc2sc(C(F)(F)F)cn2c1C(=O)NCc1ccc(N(C)C)cc1] | 382.40 |

TABLE 1-continued 5,5-heteroaromatic compounds.

| Compound ID | Structure | M.W. |
|---|---|---|
| ND-020025 | 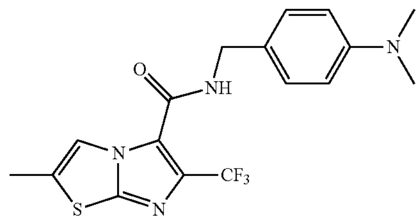 | 382.40 |
| ND-020026 | 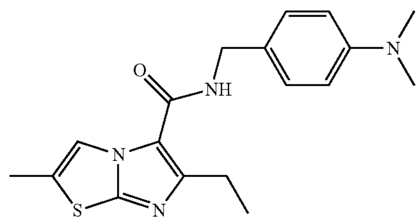 | 342.46 |
| ND-020027 | 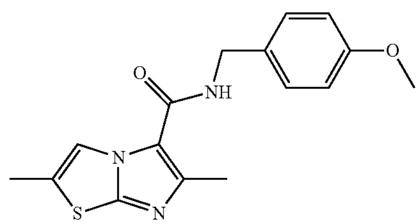 | 315.10 |
| ND-020028 | 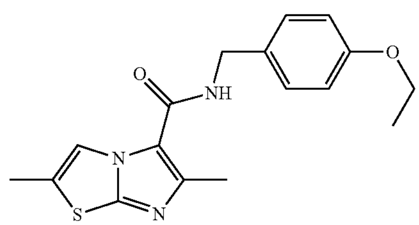 [SMILES: CCOc1ccc(CNC(=O)c2c(C)nc3sc(C)cn23)cc1] | 329.42 |
| ND-020029 | 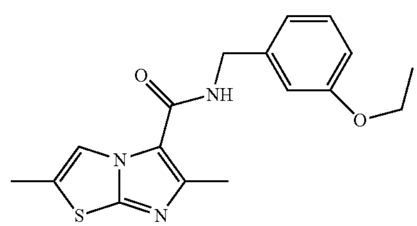 [SMILES: CCOc1cccc(CNC(=O)c2c(C)nc3sc(C)cn23)c1] | 329.42 |
| ND-020030 | 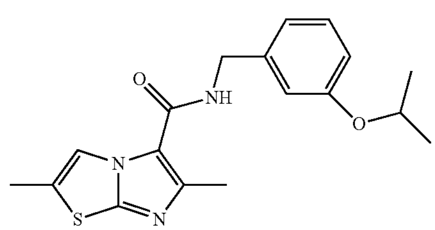 [SMILES: Cc1cn2c(C(=O)NCc3cccc(OC(C)C)c3)c(C)nc2s1] | 343.44 |
| ND-020031 | 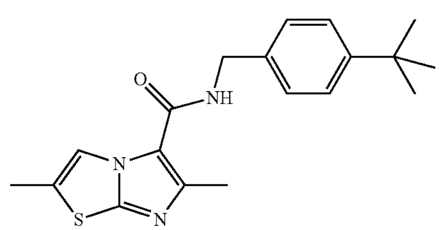 [SMILES: Cc1cn2c(C(=O)NCc3ccc(C(C)(C)C)cc3)c(C)nc2s1] | 341.47 |

TABLE 1-continued 5,5-heteroaromatic compounds.

| Compound ID | Structure | M.W. |
|---|---|---|
| ND-020032 | 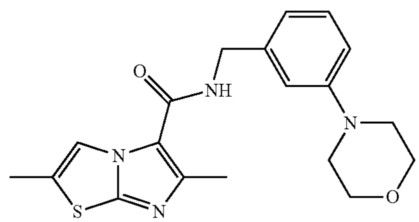 | 370.47 |
| ND-020033 | 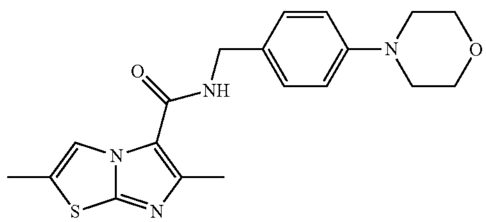 [SMILES: Cc1cn2c(C(=O)NCc3ccc(N4CCOCC4)cc3)c(C)nc2s1] | 370.47 |
| ND-020034 | 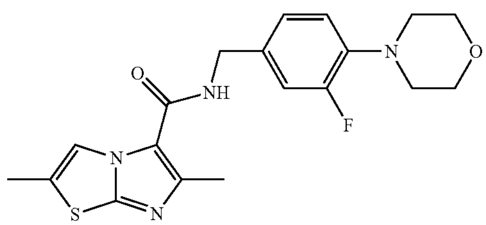 | 388.46 |
| ND-020035 | 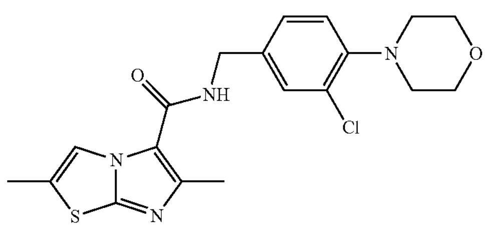 [SMILES: Cc1cn2c(C(=O)NCc3ccc(N4CCOCC4)c(Cl)c3)c(C)nc2s1] | 404.91 |
| ND-020036 | 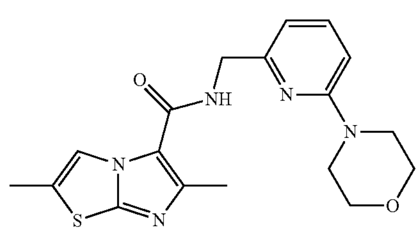 [SMILES: Cc1cn2c(C(=O)NCc3cccc(N4CCOCC4)n3)c(C)nc2s1] | 371.46 |
| ND-020037 | 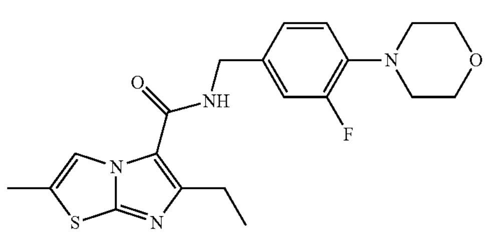 [SMILES: CCc1nc2sc(C)cn2c1C(=O)NCc1ccc(N2CCOCC2)c(F)c1] | 402.49 |

TABLE 1-continued 5,5-heteroaromatic compounds.

| Compound ID | Structure | M.W. |
|---|---|---|
| ND-020038 | 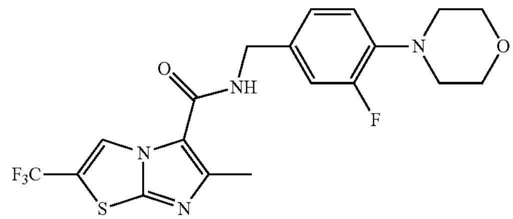 [SMILES: Cc1nc2sc(C(F)(F)F)cn2c1C(=O)NCc1ccc(N2CCOCC2)c(F)c1] | 442.43 |
| ND-020039 | 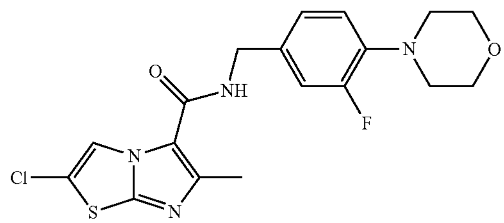 [SMILES: Cc1nc2sc(Cl)cn2c1C(=O)NCc1ccc(N2CCOCC2)c(F)c1] | 408.88 |
| ND-020040 | 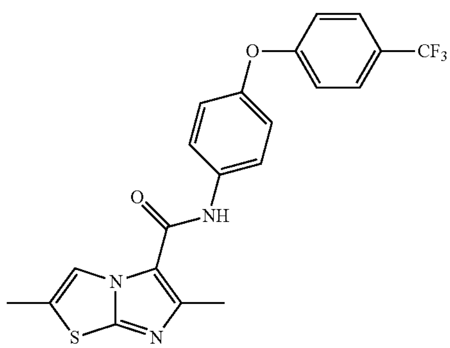 [SMILES: Cc1cn2c(C(=O)Nc3ccc(Oc4ccc(C(F)(F)F)cc4)cc3)c(C)nc2s1] | 431.33 |
| ND-020041 | 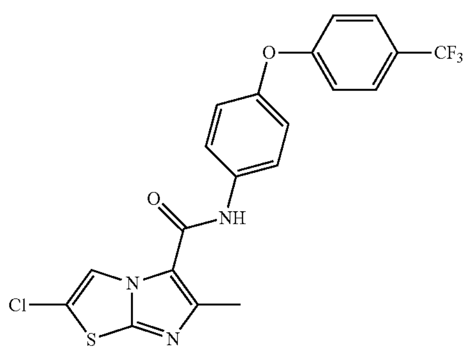 [SMILES: Cc1nc2sc(Cl)cn2c1C(=O)Nc1ccc(Oc2ccc(C(F)(F)F)cc2)cc1] | 451.85 |
| ND-020042 | 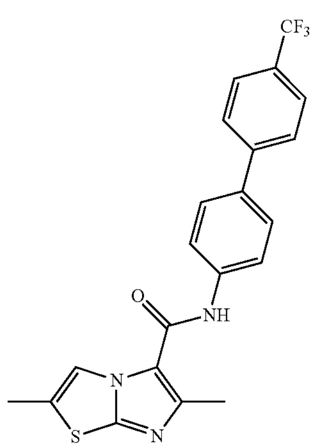 [SMILES: Cc1cn2c(C(=O)Nc3ccc(-c4ccc(C(F)(F)F)cc4)cc3)c(C)nc2s1] | 415.43 |

TABLE 1-continued 5,5-heteroaromatic compounds.

| Compound ID | Structure | M.W. |
|---|---|---|
| ND-020043 | 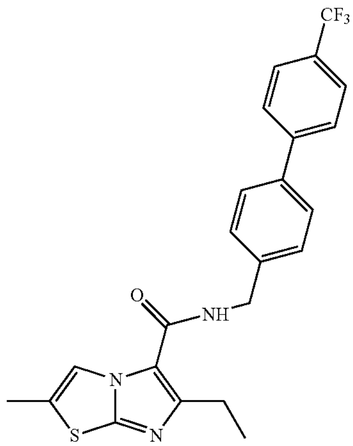 [SMILES: CCc1nc2sc(C)cn2c1C(=O)NCc1ccc(-c2ccc(C(F)(F)F)cc2)cc1] | 429.46 |
| ND-020044 | 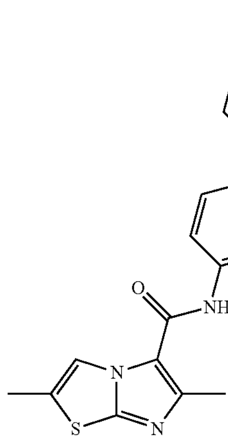 | 416.42 |
| ND-020045 | 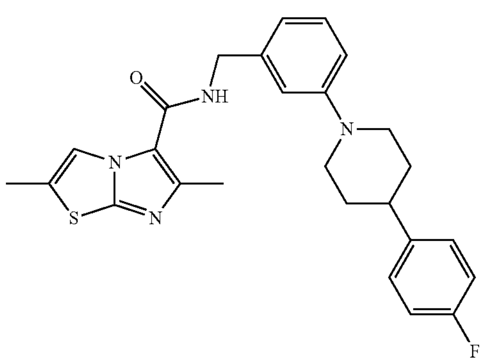 [SMILES: Cc1cn2c(C(=O)NCc3cccc(N4CCC(c5ccc(F)cc5)CC4)c3)c(C)nc2s1] | 462.58 |
| ND-020046 | 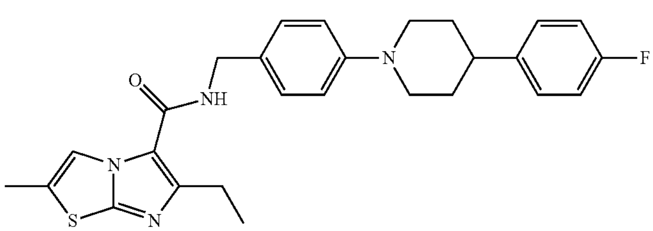 | 476.61 |

TABLE 1-continued 5,5-heteroaromatic compounds.

| Compound ID | Structure | M.W. |
|---|---|---|
| ND-020047 | 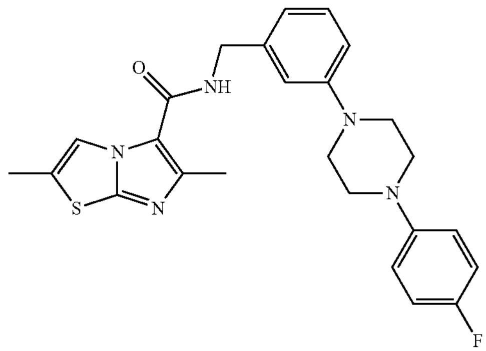 [SMILES: Cc1cn2c(C(=O)NCc3cccc(N4CCN(c5ccc(F)cc5)CC4)c3)c(C)nc2s1] | 463.57 |
| ND-020048 | 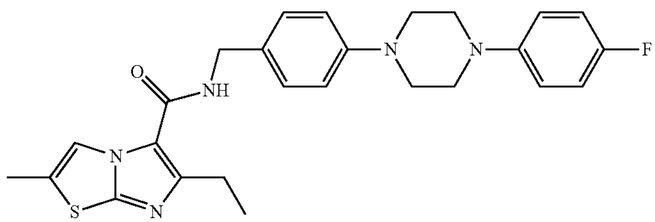 [SMILES: CCc1nc2sc(C)cn2c1C(=O)NCc1ccc(N2CCN(c3ccc(F)cc3)CC2)cc1] | 477.60 |
| ND-020049 | 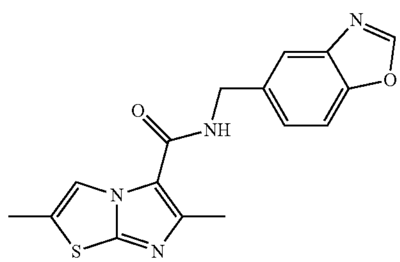 [SMILES: Cc1cn2c(C(=O)NCc3ccc4ocnc4c3)c(C)nc2s1] | 326.37 |
| ND-020050 | 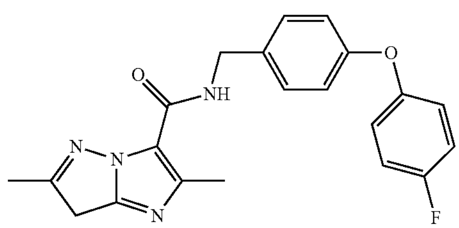 [SMILES: CC1=Nn2c(nc(C)c2C(=O)NCc2ccc(Oc3ccc(F)cc3)cc2)C1] | 378.40 |
| ND-020051 | 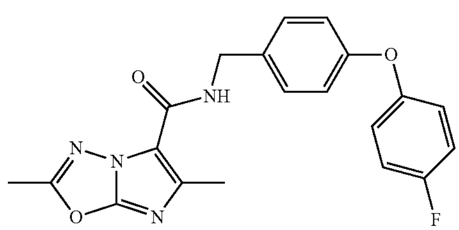 [SMILES: Cc1nn2c(C(=O)NCc3ccc(Oc4ccc(F)cc4)cc3)c(C)nc2o1] | 380.37 |
| ND-020052 | 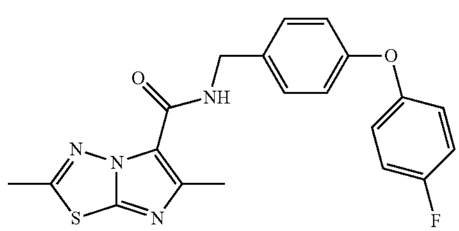 | 396.44 |

TABLE 1-continued 5,5-heteroaromatic compounds.

| Compound ID | Structure | M.W. |
|---|---|---|
| ND-020053 | 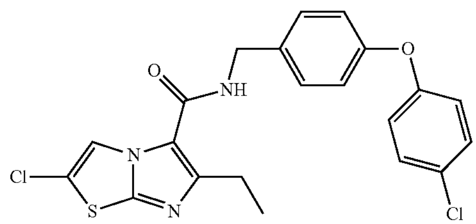 [SMILES: CCc1nc2sc(Cl)cn2c1C(=O)NCc1ccc(Oc2ccc(Cl)cc2)cc1] | 446.35 |
| ND-020054 | 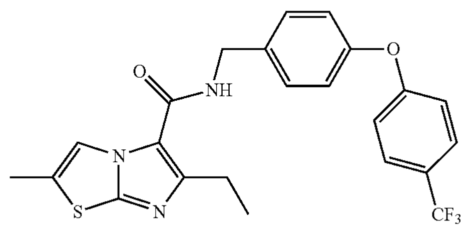 [SMILES: CCc1nc2sc(C)cn2c1C(=O)NCc1ccc(Oc2ccc(C(F)(F)F)cc2)cc1] | 459.48 |
| ND-020055 | 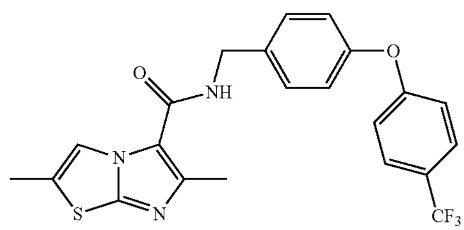 | 445.46 |
| ND-020056 | 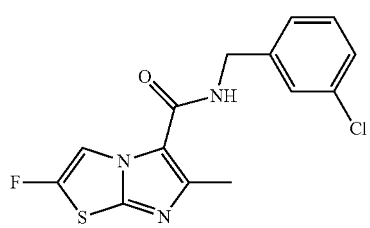 [SMILES: Cc1nc2sc(F)cn2c1C(=O)NCc1cccc(Cl)c1] | 323.77 |
| ND-020057 | 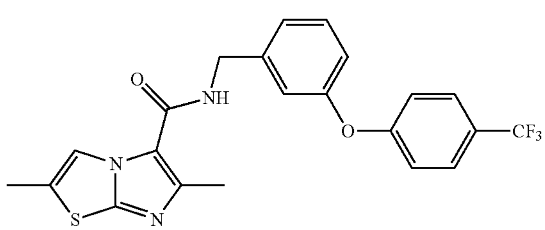 [SMILES: Cc1cn2c(C(=O)NCc3cccc(Oc4ccc(C(F)(F)F)cc4)c3)c(C)nc2s1] | 445.46 |
| ND-020058 | 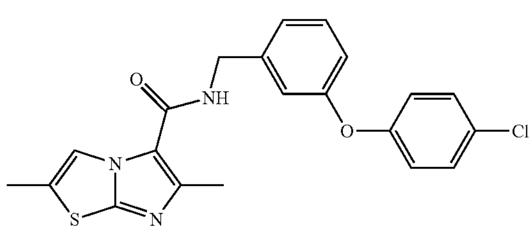 [SMILES: Cc1cn2c(C(=O)NCc3cccc(Oc4ccc(Cl)cc4)c3)c(C)nc2s1] | 411.90 |

TABLE 1-continued 5,5-heteroaromatic compounds.

| Compound ID | Structure | M.W. |
|---|---|---|
| ND-020059 | 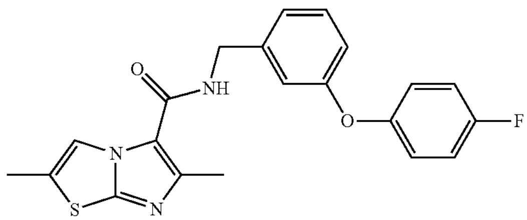 [SMILES: Cc1cn2c(C(=O)NCc3cccc(Oc4ccc(F)cc4)c3)c(C)nc2s1] | 395.45 |
| ND-020060 | 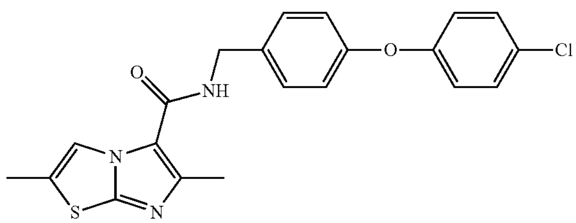 [SMILES: Cc1cn2c(C(=O)NCc3ccc(Oc4ccc(Cl)cc4)cc3)c(C)nc2s1] | 411.90 |
| ND-020061 | 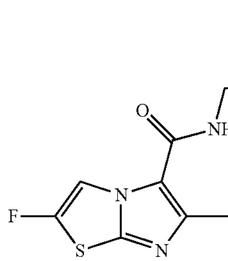 | 331.36 |
| ND-020062 | 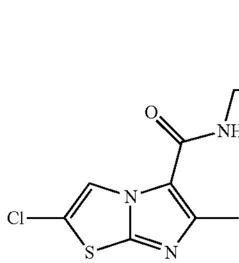 | 347.82 |
| ND-020063 | 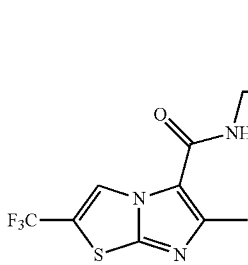 | 381.37 |
| ND-020064 | 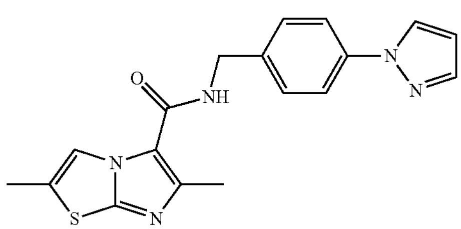 [SMILES: Cc1cn2c(C(=O)NCc3ccc(-n4cccn4)cc3)c(C)nc2s1] | 351.43 |

TABLE 1-continued 5,5-heteroaromatic compounds.

| Compound ID | Structure | M.W. |
|---|---|---|
| ND-020065 | 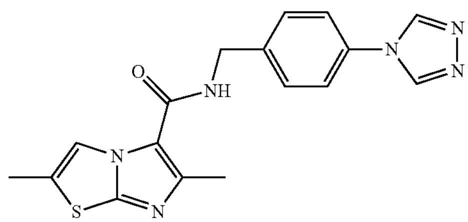 [SMILES: Cc1cn2c(C(=O)NCc3ccc(-n4cnnc4)cc3)c(C)nc2s1] | 352.11 |
| ND-020066 | 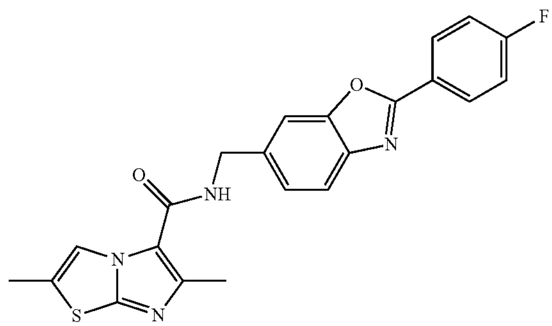 [SMILES: Cc1cn2c(C(=O)NCc3ccc4nc(-c5ccc(F)cc5)oc4c3)c(C)nc2s1] | 420.46 |
| ND-020067 | 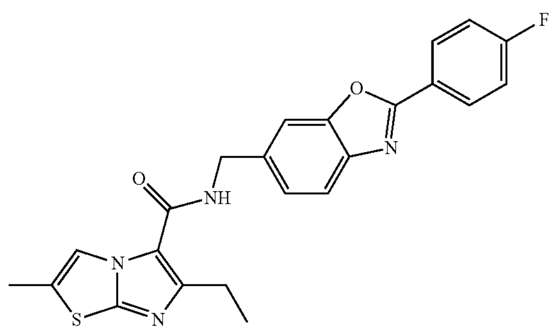 [SMILES: CCc1nc2sc(C)cn2c1C(=O)NCc1ccc2nc(-c3ccc(F)cc3)oc2c1] | 434.49 |
| ND-020068 | 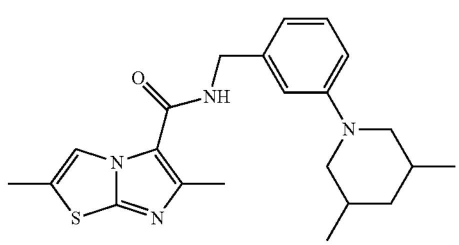 | 396.55 |
| ND-020069 | 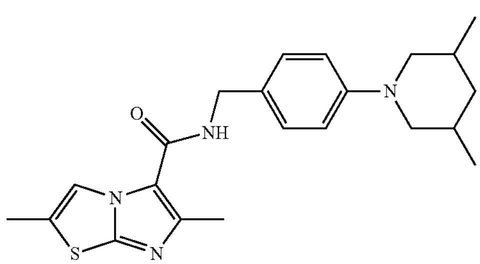 | 396.55 |

TABLE 1-continued
5,5-heteroaromatic compounds.
| Compound ID | Structure | M.W. |
|---|---|---|
| ND-020070 | 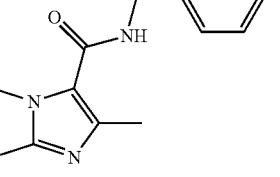 | 382.48 |
| ND-020071 | 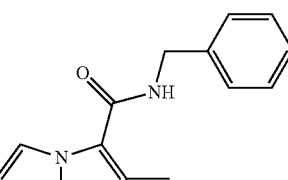 | 354.47 |
| ND-020072 | 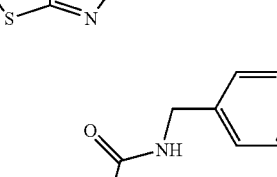 | 382.48 |
| ND-020073 | 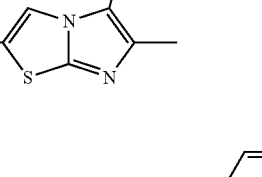 | 354.47 |
| ND-020074 | 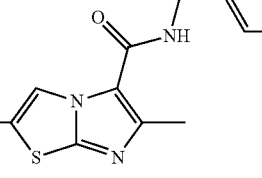 | 398.52 |
| ND-020075 | 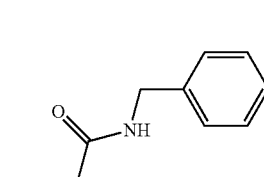 | 398.52 |

TABLE 1-continued
5,5-heteroaromatic compounds.
| Compound ID | Structure | M.W. |
|---|---|---|
| ND-020076 | 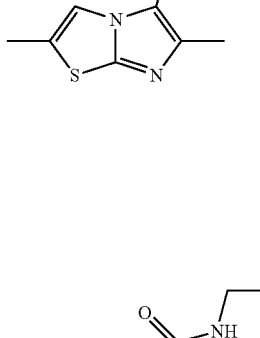 | 388.46 |
| ND-020077 | 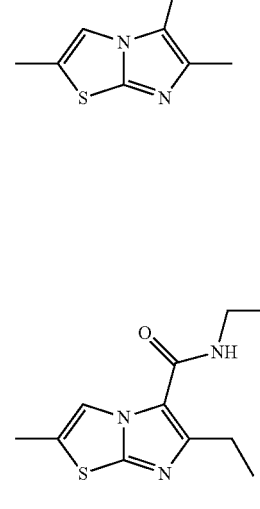 | 338.43 |
| ND-020078 | 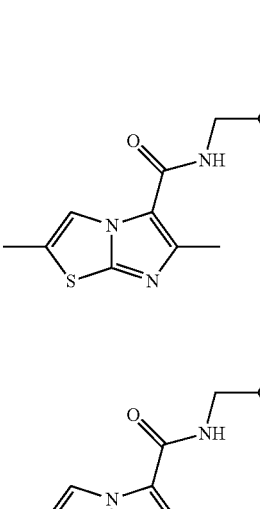 | 352.45 |
| ND-020079 | 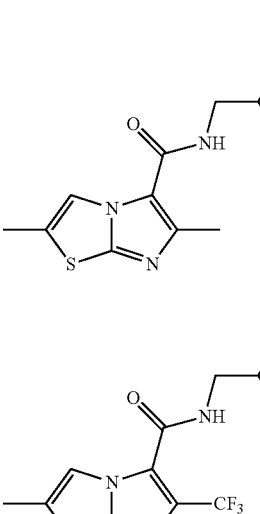 | 338.43 |
| ND-020080 | 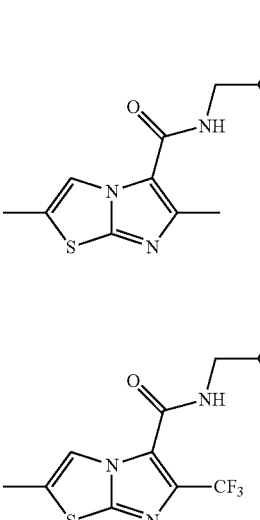 | 392.40 |

TABLE 1-continued 5,5-heteroaromatic compounds.

| Compound ID | Structure | M.W. |
|---|---|---|
| ND-020081 | 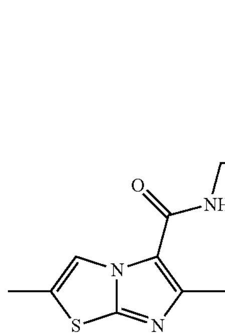 | 333.07 |

Many of the existing clinical candidates for TB therapeutics are derivatives of existing scaffolds (for instance, moxifloxacin and gatifloxacin), which results in drugs that are much more prone to emerging resistance. Other clinical candidates are complex compounds that are difficult and costly to manufacture (for example anti-TB candidates TMC207, PA-824, OPC-67683, and LL-3858). The compounds described herein provide novel and effective alternatives for killing bacteria, inhibiting bacterial growth, and for treating bacterial infections, including TB.

General Synthetic Methods

The invention relates to various 5,5 heteroaryl compounds and methods of making then. The compounds can be prepared either racemically or in enantioenriched form. Certain individual synthetic transformations for their preparation and modification are well known in the art. Many of these known techniques are elaborated in the *Compendium of Organic Synthetic Methods* (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, Jr., 1980; Vol. 5, Leroy G. Wade, Jr., 1984; and Vol. 6; as well as standard organic reference texts such as *March's Advanced Organic Chemistry: Reactions, Mechanisms, and Structure*, 5$^{th}$ Ed., by M. B. Smith and J. March (John Wiley & Sons, New York, 2001); *Comprehensive Organic Synthesis. Selectivity, Strategy & Efficiency in Modern Organic Chemistry. In 9 Volumes*, Barry M. Trost, Editor-in-Chief (Pergamon Press, New York, 1993 printing); *Advanced Organic Chemistry, Part B: Reactions and Synthesis, Second Edition*, Cary and Sundberg (1983); *Protecting Groups in Organic Synthesis, Second Edition*, Greene, T. W., and Wutz, P. G. M., John Wiley & Sons, New York; and *Comprehensive Organic Transformations*, Larock, R. C., 2$^{nd}$ Ed., John Wiley & Sons, New York (1999).

A number of exemplary methods for the preparation of the compounds and compositions of the invention are provided herein. These methods are intended to illustrate the nature of such preparations are not intended to limit the scope of applicable methods.

Generally, the reaction conditions such as temperature, reaction time, solvents, work-up procedures, and the like, will be those common in the art for the particular reaction to be performed. The cited reference material, together with material cited therein, contains detailed descriptions of such conditions. Typically the temperatures will be −100° C. to 200° C., as necessary for the reaction of interest, solvents will be aprotic or protic depending on the conditions required, and reaction times can be about 1 minute to about 2 days. Work-up typically consists of quenching any unreacted reagents followed by partition between a water/organic layer system (extraction) and separation of the layer containing the product of interest.

Oxidation and reduction reactions are typically carried out at temperatures near room temperature (about 23° C.), although for metal hydride reductions frequently the temperature is reduced to 0° C. to −100° C. Heating can also be used when appropriate. Solvents are typically aprotic for reductions and may be either protic or aprotic for oxidations. Reaction times are adjusted to achieve desired conversions.

Condensation reactions are typically carried out at temperatures near room temperature, although for non-equilibrating, kinetically controlled condensations reduced temperatures (0° C. to −100° C.) are also common. Solvents can be either protic (common in equilibrating reactions) or aprotic (common in kinetically controlled reactions). Standard synthetic techniques such as azeotropic removal of reaction by-products and use of anhydrous reaction conditions (e.g. inert gas environments) are common in the art and can be applied when applicable.

Protecting Groups. The term "protecting group", "blocking group", or "PG" refers to any group which, when bound to a hydroxy or other heteroatom prevents undesired reactions from occurring at this group and which can be removed by conventional chemical or enzymatic steps to reestablish the hydroxyl group or heteroatom. The particular removable blocking group employed is not always critical and preferred removable hydroxyl blocking groups include conventional groups such as, for example, allyl, benzyl, acetyl, chloroacetyl, thiobenzyl, benzylidene, phenacyl, methyl methoxy, silyl ethers (e.g., trimethylsilyl (TMS), t-butyl-diphenylsilyl (TBDPS), or t-butyldimethylsilyl (TBS)) and any other group that can be introduced chemically onto a hydroxyl functionality and later selectively removed either by chemical or enzymatic methods in mild conditions compatible with the nature of the product. The R groups of various schemes and formulas herein can also be protecting groups, such as the protecting groups described above and in various literature cited herein.

Suitable protecting groups are known to those skilled in the art and disclosed in more detail by T. W. Greene, *Protecting Groups In Organic Synthesis*; Wiley: New York, 1981 ("Greene") and the references cited therein, and by Kocienski, Philip J.; *Protecting Groups* (Georg Thieme Verlag Stuttgart, New York, 1994), both of which are incorporated herein by reference.

Protecting groups are available, commonly known and used, and are optionally used to prevent side reactions with the protected group during synthetic procedures, i.e. routes or methods to prepare various compounds by the methods described herein. For the most part the decision as to which groups to protect, when to install and remove the protecting groups, and the nature of the chemical protecting group "PG" will be dependent upon the chemistry of the reaction to be protected against (e.g., acidic, basic, oxidative, reductive or other conditions) and the intended product of the synthesis.

Protecting groups do not need to be, and generally are not, the same if the compound is substituted with multiple PGs. In general, PG will be used to protect functional groups such as carboxyl, hydroxyl, thio, or amino groups and to thus prevent side reactions or to otherwise facilitate the synthetic efficiency. The order of deprotection to yield free, deprotected groups can be dependent upon the intended products of the synthesis and the reaction conditions to be encountered, and may occur in any order as determined by the artisan.

Various functional groups of the compounds of the invention may be protected. For example, protecting groups for —OH groups (whether hydroxyl, carboxylic acid, or other functions) include "ether- or ester-forming groups". Many ether- or ester-forming groups are capable of functioning as chemical protecting groups in the synthetic schemes set forth herein. However, some hydroxyl and thio protecting groups are neither ether- nor ester-forming groups, as will be understood by those skilled in the art. For further detail regarding carboxylic acid protecting groups and other protecting groups for acids, see Greene, cited above. Such groups include by way of example and not limitation, amides, hydrazides, and the like.

As to any of the compounds and formulas described herein, which contain one or more substituents, it is understood, of course, that such groups do not contain any substitution or substitution patterns that are sterically impractical and/or synthetically non-feasible. It will be appreciated that the compounds on may contain asymmetrically substituted carbon atoms and thus may be prepared and isolated in either optically active or racemic forms. All chiral, diastereomeric, and racemic forms and all geometric isomeric forms of the compounds described herein, individually and/or collectively, are part of this invention.

One diastereomer may display superior activity compared to another. When required, separation of racemic materials can be achieved by high performance liquid chromatography (HPLC) using a chiral column or by a resolution using a resolving agent such as camphonic chloride, as in Thomas J. Tucker et al., J. Med. Chem. 1994, 37, 2437-2444. A chiral compound may also be directly synthesized using a chiral catalyst or a chiral ligand (see, for example, Mark A. Huffman, et al., J. Org. Chem. 1995, 60, 1590-1594) or by the techniques described herein.

In general, modifications to the compounds and formulas described herein can be made according to organic synthesis techniques known to those of skill in the art and/or according to the synthetic schemes provided herein. Where desired, synthesis of a subject compound can begin with commercially available chemicals, from compounds described in the chemical literature, or from products of the reactions and methods described herein. Commercially available compounds may be obtained from standard commercial sources including Acros Organics (Pittsburgh Pa.), Aldrich Chemical (Milwaukee Wis., including Sigma Chemical and Fluka), Eastman Organic Chemicals, Eastman Kodak Company (Rochester N.Y.), Fisher Scientific Co. (Pittsburgh Pa.), ICN Biomedicals, Inc. (Costa Mesa Calif.), Lancaster Synthesis (Windham N.H.), TCI America (Portland Oreg.), and Wako Chemicals USA, Inc. (Richmond Va.).

Pharmaceutical Formulations

The compounds described herein can be used to prepare therapeutic pharmaceutical compositions, for example, by combining the compounds with a pharmaceutically acceptable diluent, excipient, or carrier. The compounds may be added to a carrier in the form of a salt or solvate. For example, in cases where compounds are sufficiently basic or acidic to form stable nontoxic acid or base salts, administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartrate, succinate, benzoate, ascorbate, α-ketoglutarate, and β-glycerophosphate. Suitable inorganic salts may also be formed, including hydrochloride, halide, sulfate, nitrate, bicarbonate, and carbonate salts.

Pharmaceutically acceptable salts may be obtained using standard procedures well known in the art, for example by reacting a sufficiently basic compound such as an amine with a suitable acid to provide a physiologically acceptable ionic compound. Alkali metal (for example, sodium, potassium or lithium) or alkaline earth metal (for example, calcium) salts of carboxylic acids can also be prepared by analogous methods.

The compounds of the formulas described herein can be formulated as pharmaceutical compositions and administered to a mammalian host, such as a human patient, in a variety of forms. The forms can be specifically adapted to a chosen route of administration, e.g., oral or parenteral administration, by intravenous, intramuscular, topical or subcutaneous routes.

The compounds described herein may be systemically administered in combination with a pharmaceutically acceptable vehicle, such as an inert diluent or an assimilable edible carrier. For oral administration, compounds can be enclosed in hard or soft shell gelatin capsules, compressed into tablets, or incorporated directly into the food of a patient's diet. Compounds may also be combined with one or more excipients and used in the form of ingestible tablets, buccal tablets, troches, capsules, elixirs, suspensions, syrups, wafers, and the like. Such compositions and preparations typically contain at least 0.1% of active compound. The percentage of the compositions and preparations can vary and may conveniently be from about 0.5% to about 60%, about 1% to about 25%, or about 2% to about 10%, of the weight of a given unit dosage form. The amount of active compound in such therapeutically useful compositions can be such that an effective dosage level can be obtained.

The tablets, troches, pills, capsules, and the like may also contain one or more of the following: binders such as gum tragacanth, acacia, corn starch or gelatin; excipients such as dicalcium phosphate; a disintegrating agent such as corn starch, potato starch, alginic acid and the like; and a lubricant such as magnesium stearate. A sweetening agent such as sucrose, fructose, lactose or aspartame; or a flavoring agent such as peppermint, oil of wintergreen, or cherry flavoring, may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propyl parabens as preservatives, a dye and flavoring such as cherry or orange flavor. Any material used in preparing any unit dosage form should be pharmaceutically acceptable and substantially non-toxic in the amounts employed. In addition, the active compound may be incorporated into sustained-release preparations and devices.

The active compound may be administered intravenously or intraperitoneally by infusion or injection. Solutions of the active compound or its salts can be prepared in water, optionally mixed with a nontoxic surfactant. Dispersions can be prepared in glycerol, liquid polyethylene glycols, triacetin, or mixtures thereof, or in a pharmaceutically acceptable oil. Under ordinary conditions of storage and use, preparations may contain a preservative to prevent the growth of microorganisms.

Pharmaceutical dosage forms suitable for injection or infusion can include sterile aqueous solutions, dispersions, or sterile powders comprising the active ingredient adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions, or by the use of surfactants. The prevention of the action of microorganisms can be brought about by various antibacterial and/or antifungal agents, for example, parabens, chlorobutanol, phenol, sorbic acid, thimerosal, and the like. In many cases, it will be preferable to include isotonic agents, for example, sugars, buffers, or sodium chloride. Prolonged absorption of the injectable compositions can be brought about by agents delaying absorption, for example, aluminum monostearate and/or gelatin.

Sterile injectable solutions can be prepared by incorporating the active compound in the required amount in the appropriate solvent with various other ingredients enumerated above, as required, optionally followed by filter sterilization. In the case of sterile powders for the preparation of sterile injectable solutions, methods of preparation can include vacuum drying and freeze drying techniques, which yield a powder of the active ingredient plus any additional desired ingredient present in the solution.

For topical administration, compounds may be applied in pure form, e.g., when they are liquids. However, it will generally be desirable to administer the active agent to the skin as a composition or formulation, for example, in combination with a dermatologically acceptable carrier, which may be a solid, a liquid, a gel, or the like.

Useful solid carriers include finely divided solids such as talc, clay, microcrystalline cellulose, silica, alumina, and the like. Useful liquid carriers include water, dimethyl sulfoxide (DMSO), alcohols, glycols, or water-alcohol/glycol blends, in which a compound can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using a pump-type or aerosol sprayer.

Thickeners such as synthetic polymers, fatty acids, fatty acid salts and esters, fatty alcohols, modified celluloses, or modified mineral materials can also be employed with liquid carriers to form spreadable pastes, gels, ointments, soaps, and the like, for application directly to the skin of the user.

Examples of dermatological compositions for delivering active agents to the skin are known to the art; for example, see U.S. Pat. No. 4,992,478 (Geria), U.S. Pat. No. 4,820,508 (Wortzman), U.S. Pat. No. 4,608,392 (Jacquet et al.), and U.S. Pat. No. 4,559,157 (Smith et al.). Such dermatological compositions can be used in combinations with the compounds described herein where an ingredient of such compositions can optionally be replaced by a compound described herein, or a compound described herein can be added to the composition Useful dosages of the compounds described herein can be determined by comparing their in vitro activity, and in vivo activity in animal models. Methods for the extrapolation of effective dosages in mice, and other animals, to humans are known to the art; for example, see U.S. Pat. No. 4,938,949 (Borch et al.). The amount of a compound, or an active salt or derivative thereof, required for use in treatment will vary not only with the particular compound or salt selected but also with the route of administration, the nature of the condition being treated, and the age and condition of the patient, and will be ultimately at the discretion of an attendant physician or clinician.

The compound can be conveniently administered in a unit dosage form, for example, containing 5 to 1000 mg/m$^2$, conveniently 10 to 750 mg/m$^2$, most conveniently, 50 to 500 mg/m$^2$ of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The compounds described herein can be effective antimicrobial agents, for example, against various microbes that cause TB. The invention provides therapeutic methods of treating bacterial and/or TB infections in a mammal, which involve administering to a mammal having an infection an effective amount of a compound or composition described herein. A mammal includes a primate, human, rodent, canine, feline, bovine, ovine, equine, swine, caprine, bovine and the like.

The ability of a compound of the invention to kill a microbe or bacteria, to inhibit its growth, and/or to treat a related infection may be determined by using assays well known to the art. For example, the design of treatment protocols, toxicity evaluation, data analysis, quantification of cell kill, and the biological significance of the use of various screens are known. In addition, ability of a compound to treat an infection may be determined using the Tests described below.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1

Preparation of the 5,5-Heteroaromatics and ND-010081

The compounds described herein may be synthesized according to the following general procedures. ND-010081, for example, can be made in a few synthetic steps from readily available, inexpensive reagents. To evaluate the potential availability and affordability of making this compound on a multigram scale, ND-010081 was prepared on a kilogram scale using the following procedure (Scheme 1, below).

Scheme 1. Multi-gram synthesis of ND-010081.

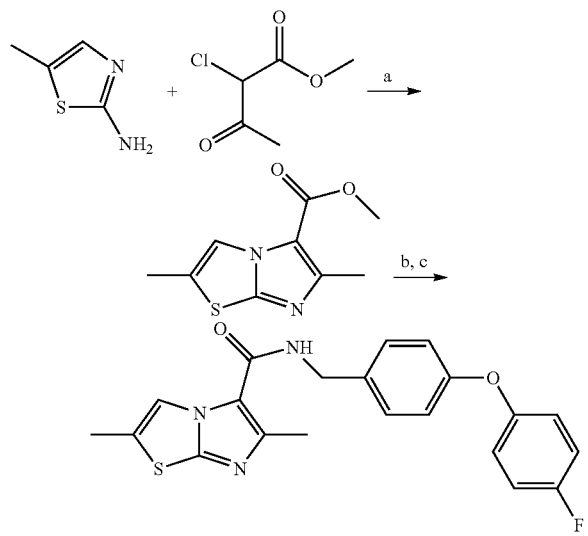

Reagents: a) 1,2-dimethoxyethane, NaHCO3, reflux, 24 hours; (b) 1N LiOH, EtOH, reflux, 20 hours; (c) EDC—HCl, DMAP, and 4-(4-fluorophenoxy) benzylamine hydrochloride, 16 hours.

In this specific example of the synthesis of ND-010081, a solution of 2-amino-5-methylthiazole (5.0 g, 42.9 mmol) and 2-chloroacetoacetic acid methyl ester (2.75 mL, 21.5 mmol) in dry 1,2-dimethoxyethane (45 ml) was heated at reflux for 48 hours under argon. The resulting solids were removed from solution by filtration and solvent was removed under reduced pressure, and the orange oil residue was recrystallized from ethanol or purified by silica gel column chromatography eluting with $CH_2Cl_2$/EtOAc (2:1) to give product methyl 2,6-dimethylimidazo[2,1-b]thiazole-5-carboxylate (1.6 g, 36%). $^1$H NMR (300 MHz, CDCl$_3$) δ ppm 3.91 (3H, s), 2.58 (3H, s), 2.44 (3H, d, J=1.35 Hz), 7.76 (1H, m).

The methyl 2,6-dimethylimidazo[2,1-b]thiazole-5-carboxylate (1.55 g, 7.4 mmol) was dissolved in 15 mL of ethanol (95%) and 1 N LiOH added (7 mL, 7 mmol) was added and reaction was heated to reflux for 20 hours. The resulting solution was concentrated to dryness and then made acidic (pH~3) with the addition of 4N HCl; resulting solids were collected by filtration and rigorously dried to give 1.1 grams of 2,6-dimethylimidazo[2,1-b]thiazole-5-carboxylic acid an off white solid. The 2,6-dimethylimidazo[2,1-b]thiazole-5-carboxylic acid (0.2 grams, 0.96 mmol) was dissolved in 6 mL acetonitrile followed by 1-ethyl-3-(3-dimethylaminopropyl) carbodiimide hydrochloride (EDC-HCl, 186 mg, 0.96 mmol), 4-dimethylaminopyridine (DMAP, 118 mg, 0.096) and 4-(4-fluorophenoxyl)benzylamine hydrochloride (270 mg, 1.06 mmol). This reaction was stirred at room temperature under argon for 16 hours. The reaction mixture was concentrated to dryness and was dissolved in $CH_2Cl_2$ and washed with saturated sodium bicarbonate solution (2×), dilute acidic acid solution (2×) and brine washed. Organics were dried over $Na_2SO_4$, the drying agent was filtered off, and organics were concentrated down to an orange solid. The solid was either recrystallized from hot acetonitrile or purified through a silica gel column eluting with a gradient of 1:10 (EtOAc:$CH_2Cl_2$) to 10:1 (EtOAc:$CH_2Cl_2$) to give 225 mg of N-(4-(4-chlorophenoxy)benzyl)-2,6-dimethylimidazo[2,1-b]thiazole-5-carboxamide (ND-010081) as an off white solid in 59% yield. $^1$H NMR (300 MHz, CDCl$_3$) δ ppm 4.62 (2H, d, J=5.8 Hz), 2.56 (3H, s), 2.43 (3H, d, J=1.3 Hz), 7.98 (1H, m), 7.31 (2H, d, J=8.7 Hz), 7.08-6.90 (6H, m).

An X-ray crystal structure was determined for N-(4-(4-chlorophenoxy)benzyl)-2,6-dimethylimidazo[2,1-b]thiazole-5-carboxamide (FIG. 1). Crystal data for $C_{21}H_{18}FN_3O_2S$; $M_r$=395.44; Triclinic; space group P-1; a=9.7959 (12) Å; b=11.1380(14) Å; c=18.287(2) Å; α=81.961(3)°; β=86.418(3)°; γ=75.515(3)°; V=1912.1(4) Å$^3$; Z=4; T=200(2) K; λ(Mo–Kα)=0.71073 Å; μ(Mo–Kα)= 0.201 mm$^{-1}$; $d_{calc}$=1.374 g·cm$^{-3}$; 31413 reflections collected; 9091 unique ($R_{int}$=0.0334); giving $R_1$=0.0471, $wR_2$=0.1153 for 5320 data with [I>2σ(I)] and $R_1$=0.0914, $wR_2$=0.1306 for all 9091 data. Residual electron density (e$^-$·Å$^{-3}$) max/min: 0.271/−0.328.

For the structure of FIG. 1, an arbitrary sphere of data were collected on a colorless rod-like crystal, having approximate dimensions of 0.42×0.15×0.06 mm, on a Bruker Kappa X8-APEX-II diffractometer using a combination of ω- and φ-scans of 0.5°. Data were corrected for absorption and polarization effects and analyzed for space group determination. The structure was solved by direct methods and expanded routinely. The model was refined by full-matrix least-squares analysis of F$^2$ against all reflections. All non-hydrogen atoms were refined with anisotropic thermal displacement parameters. Unless otherwise noted, hydrogen atoms were included in calculated positions. Thermal parameters for the hydrogens were tied to the isotropic thermal parameter of the atom to which they are bonded (1.5× for methyl, 1.2× for all others).

Example 2

Preparation of Various Compounds of the Invention

The general synthetic procedure used to prepare the various 5,5-heterocyclic derivatives ("ITA" for imidazo[2,1-b]thiazole-5-carboxamide, "IOA" for imidazo[2,1-b]oxazole-5-carboxamide, "ITDA" for imidazo[2,1-b][1,3,4]thiadiazole-5-carboxamide, "IODA" for imidazo[2,1-b][1,3,4]oxadiazole-5-carboxamide, "PIA" for pyrrolo[1,2-a]imidazole-3-carboxamide, "IPYA" for imidazo[1,2-b]pyrazole-3-carboxamides) as follows:

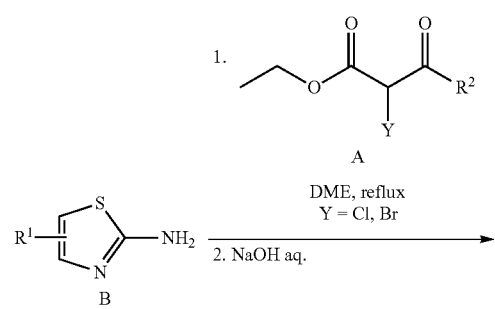
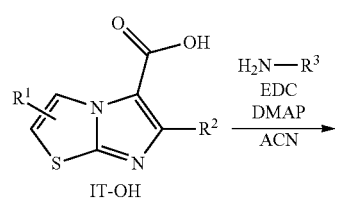
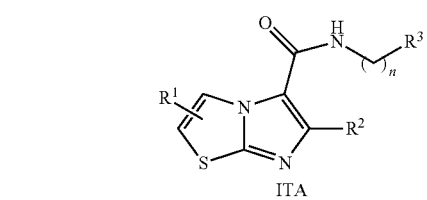
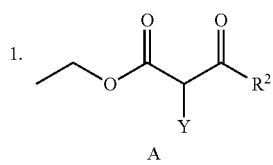
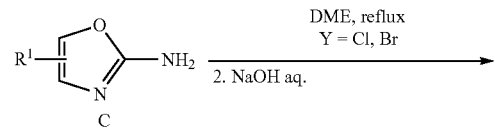
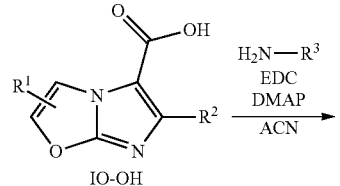
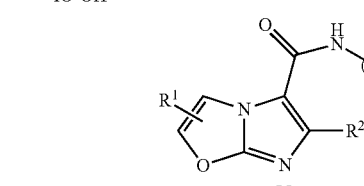
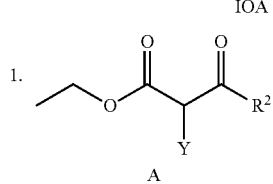
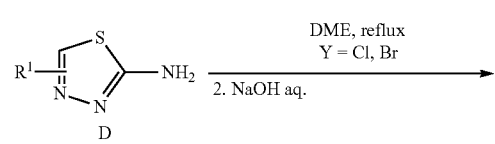
-continued
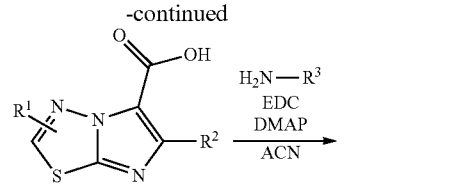
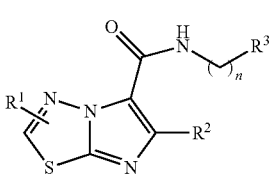
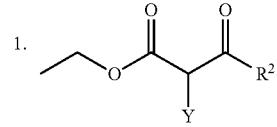
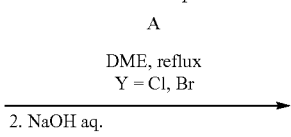
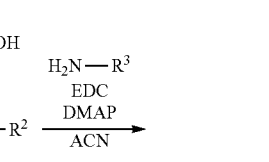
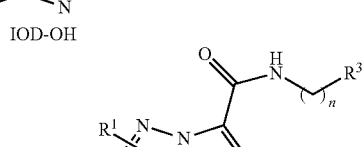
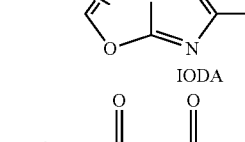
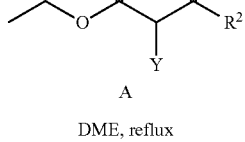
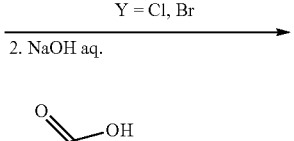
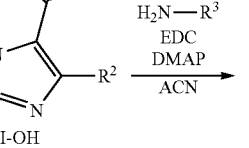
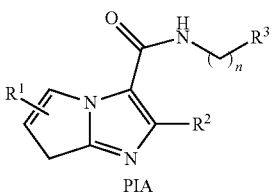

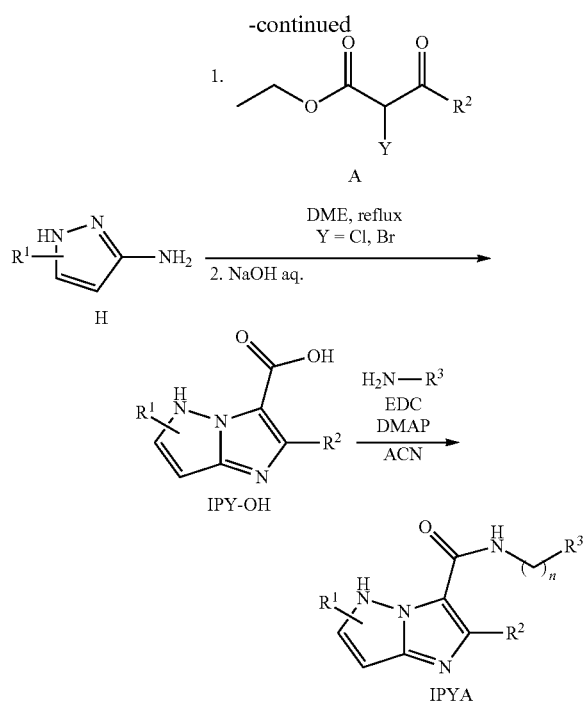

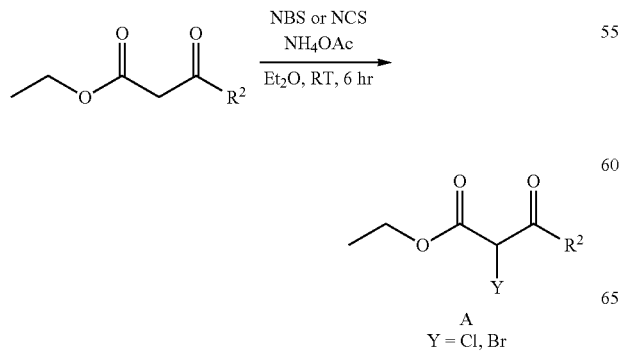

Six different carboxylic acid intermediates can be prepared (IT-OH, IO-OH, ITD-OH, IOD-OH, PA-OH, IPY-OH), which were elaborated into a focused set of anti-tubercular agents ("ITA" for imidazo[2,1-b]thiazole-5-carboxamide, "IOA" for imidazo[2,1-b]oxazole-5-carboxamide, "ITDA" for imidazo[2,1-b][1,3,4]thiadiazole-5-carboxamide, "IODA" for imidazo[2,1-b][1,3,4]oxadiazole-5-carboxamide, "PIA" for pyrrolo[1,2-a]imidazole-3-carboxamide, "IPYA" for imidazo[1,2-b]pyrazole-3-carboxamide) of the generalized structure shown. These compounds were easily made in straightforward two step syntheses in good overall yields. First, reaction of the appropriately substituted amino-heterocycle (B, C, D, E, F, or H) with ethyl 2-chloroacetoacetate (or any reagent of structure A) in an appropriate solvent like 1,2-dimethoxyethane or ethanol followed by saponification with sodium hydroxide and acidic work up gave the free acids (IT-OH, IO-OH, ITD-OH, IOD-OH, PA-OH, IPY-OH). Then these carboxylic acid intermediates were all readily converted to various amide analogs (ITA, IOA, ITDA, IODA, PIA and IPYA) through classical EDC-mediated coupling reactions in good yields Reagents of structure A can be prepared by the methods of Organic Syntheses, Coll. Vol. 4, p. 590 (1963); Vol. 33, p. 43 (1953) and WO 2011/113606.

Substituted pyrazol-3-amine heterocycles (H) are in limited commercial availability but can be prepared by a modified procedure from Organic Syntheses, Vol. 89, p. 537 (2012) wherein hydrazine is reacted with 3-aminobut-2-enenitrile in basic conditions to give pyrazol-3-amines of structure H.

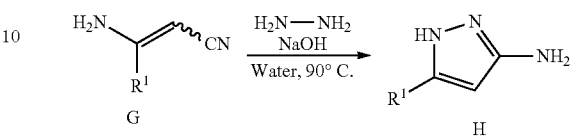

The various NH—R³ (preferably substituted benzyl amines, "—NH—CH₂-phenyl") used are commercially available but all can be prepared synthetically.

The general synthesis of 4, 4a, 4', 4'a, 4" (benzyl amines substituted with various cycloheteroalkyls (heterocycles) like morpholine, piperdine and piperzine at various positions).

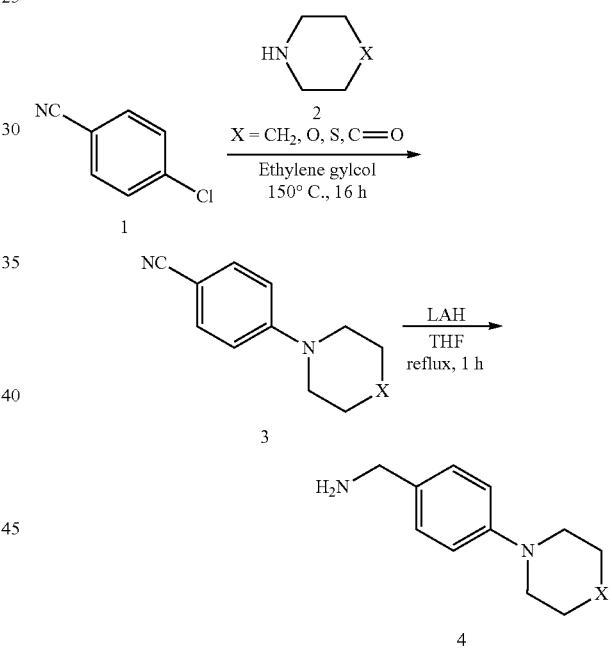

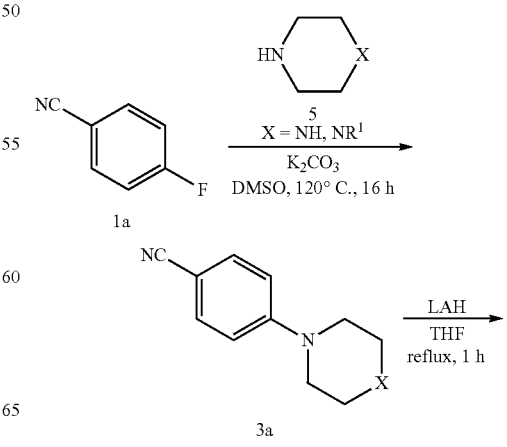

-continued
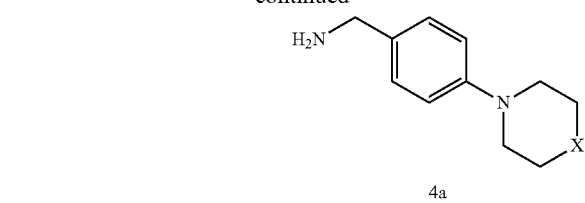
4a
As described in WO 2011/113606 and in part by "Reproducibility and Scalability of Microwave-Assisted Reactions," DOI: 10.5772/19952 by De La Hoz et al.
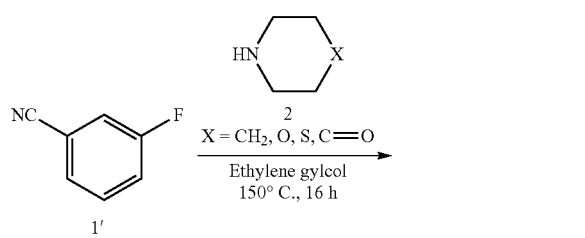
1'
X = CH$_2$, O, S, C=O
Ethylene gylcol
150° C., 16 h
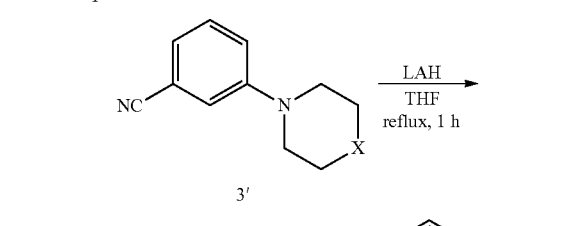
3'
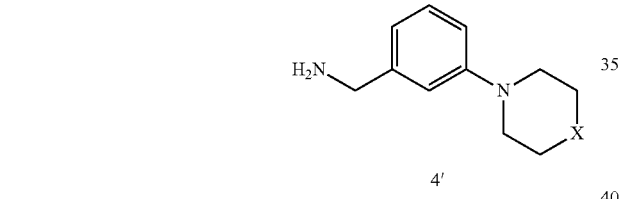
4'
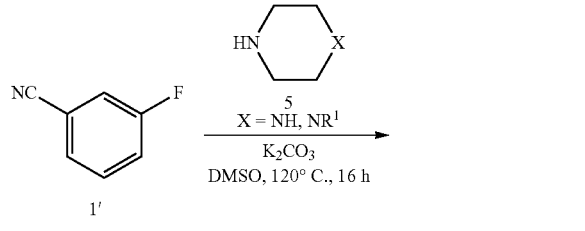
1'
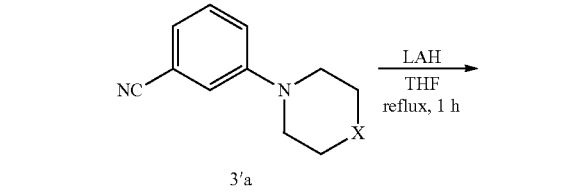
3'a
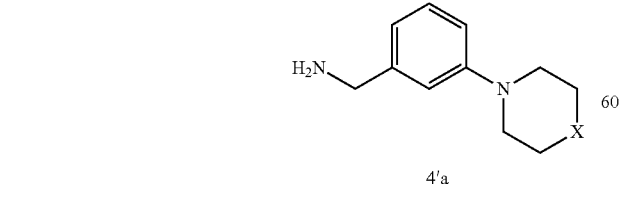
4'a
As described in Tet. Lett. 1999 40 (6), pp 1219-1222.
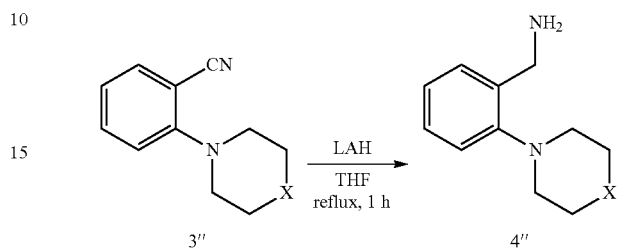
1''
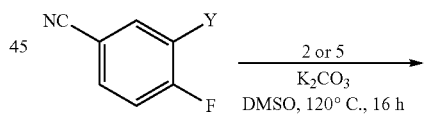
3''        4''
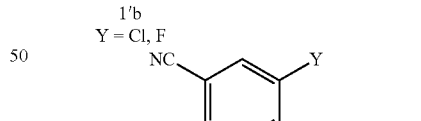
1''a
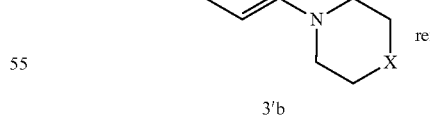
3''        4''
As described in Tet. Lett. 2005 46 (15), pp 2571-2575 (for the former) and U.S. Pat. No. 6,689,882 (for the latter).
1'b
Y = Cl, F
3'b
4'b
As described in Tet. Lett. 1999 40 (6), pp 1219-1222.

The substituted benzyl amines of general structure 4, 4a, 4', 4'a, 4", 4'b can be elaborated into compounds ND-020032 and ND-020033 and the like through the following scheme:
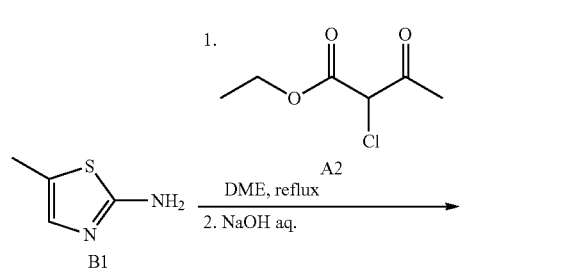
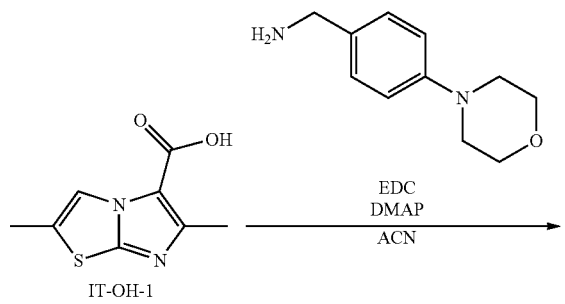
ND-020032
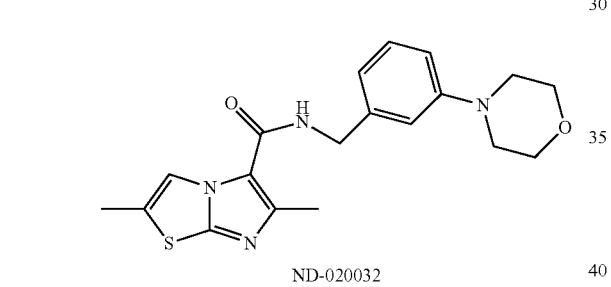
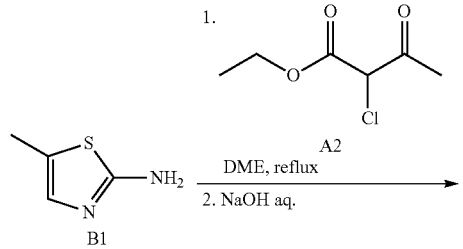
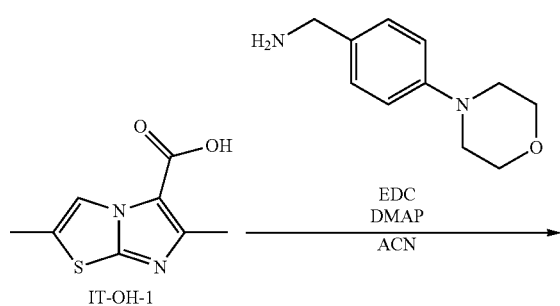
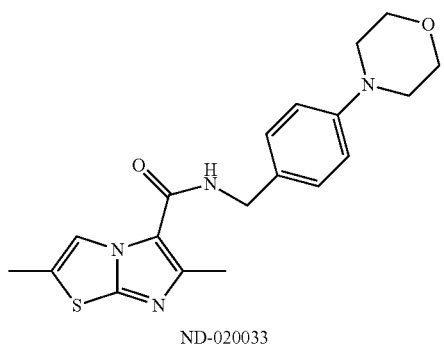
ND-020033
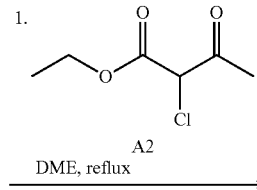
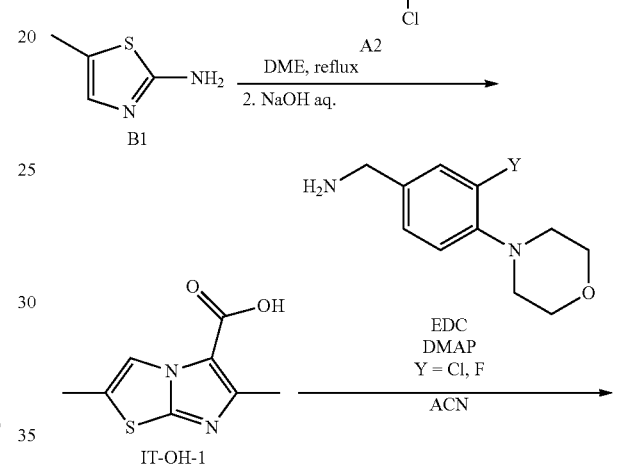
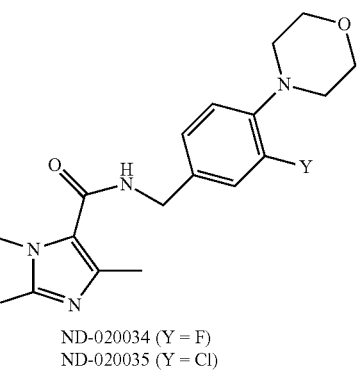
ND-020034 (Y = F)
ND-020035 (Y = Cl)
The general synthesis of substituted biaryl ether benzyl amines 9 and 13:
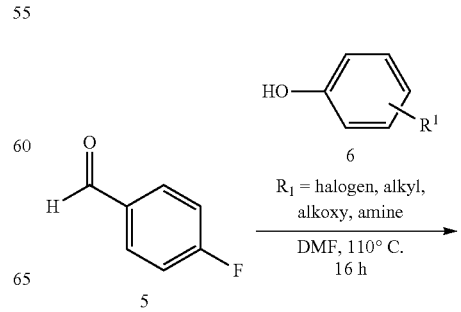
$R_1$ = halogen, alkyl, alkoxy, amine

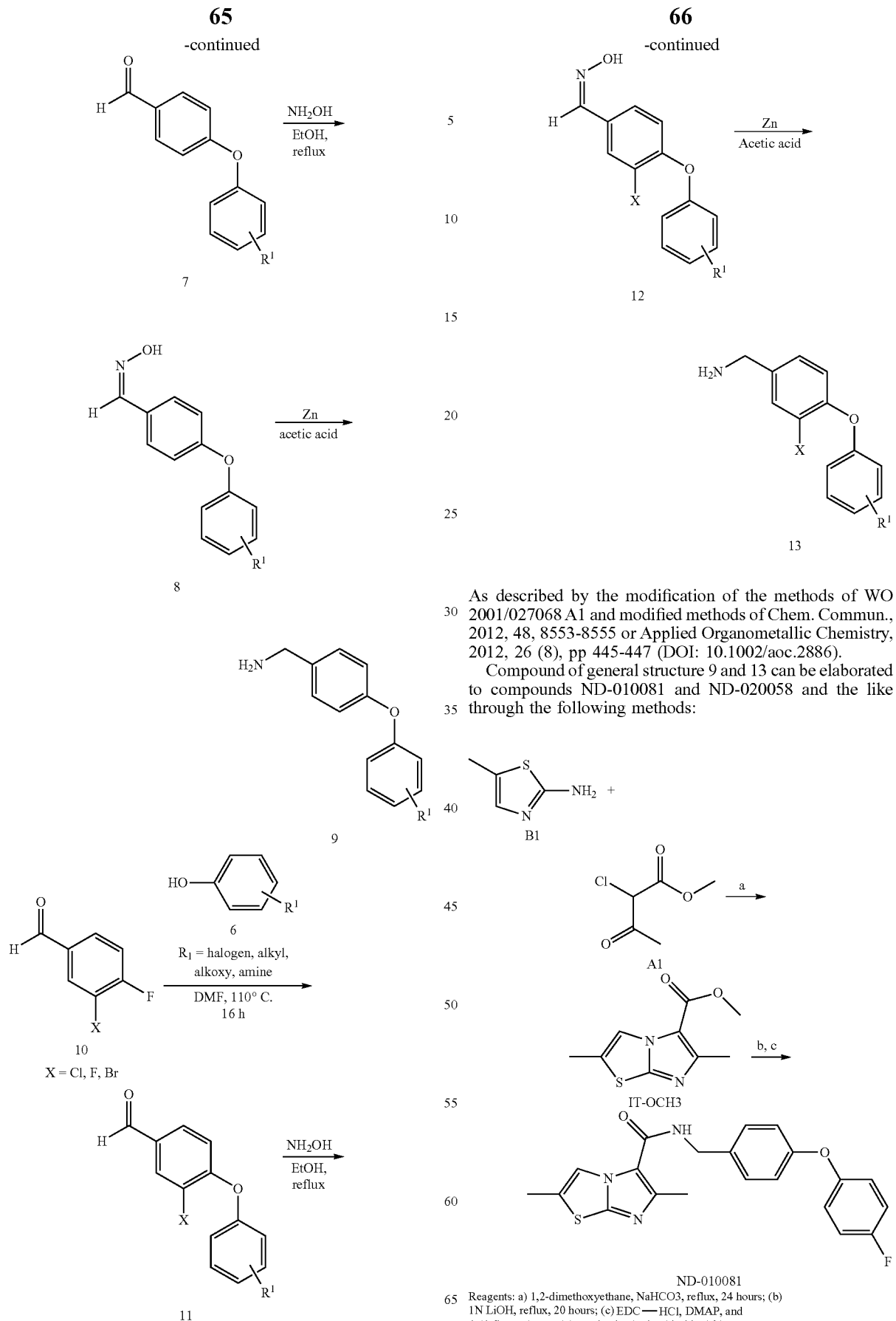

As described by the modification of the methods of WO 2001/027068 A1 and modified methods of Chem. Commun., 2012, 48, 8553-8555 or Applied Organometallic Chemistry, 2012, 26 (8), pp 445-447 (DOI: 10.1002/aoc.2886).

Compound of general structure 9 and 13 can be elaborated to compounds ND-010081 and ND-020058 and the like through the following methods:

Reagents: a) 1,2-dimethoxyethane, NaHCO3, reflux, 24 hours; (b) 1N LiOH, reflux, 20 hours; (c) EDC—HCl, DMAP, and 4-(4-fluorophenoxy) benzylamine hydrochloride, 16 hours.

Using the methods described for preparing ND-010081 (Example 1 above), additional compounds like ND-020058 can be prepared when 3-(4-chlorophenoxy)benzylamine; CAS no: 154108-30-2:

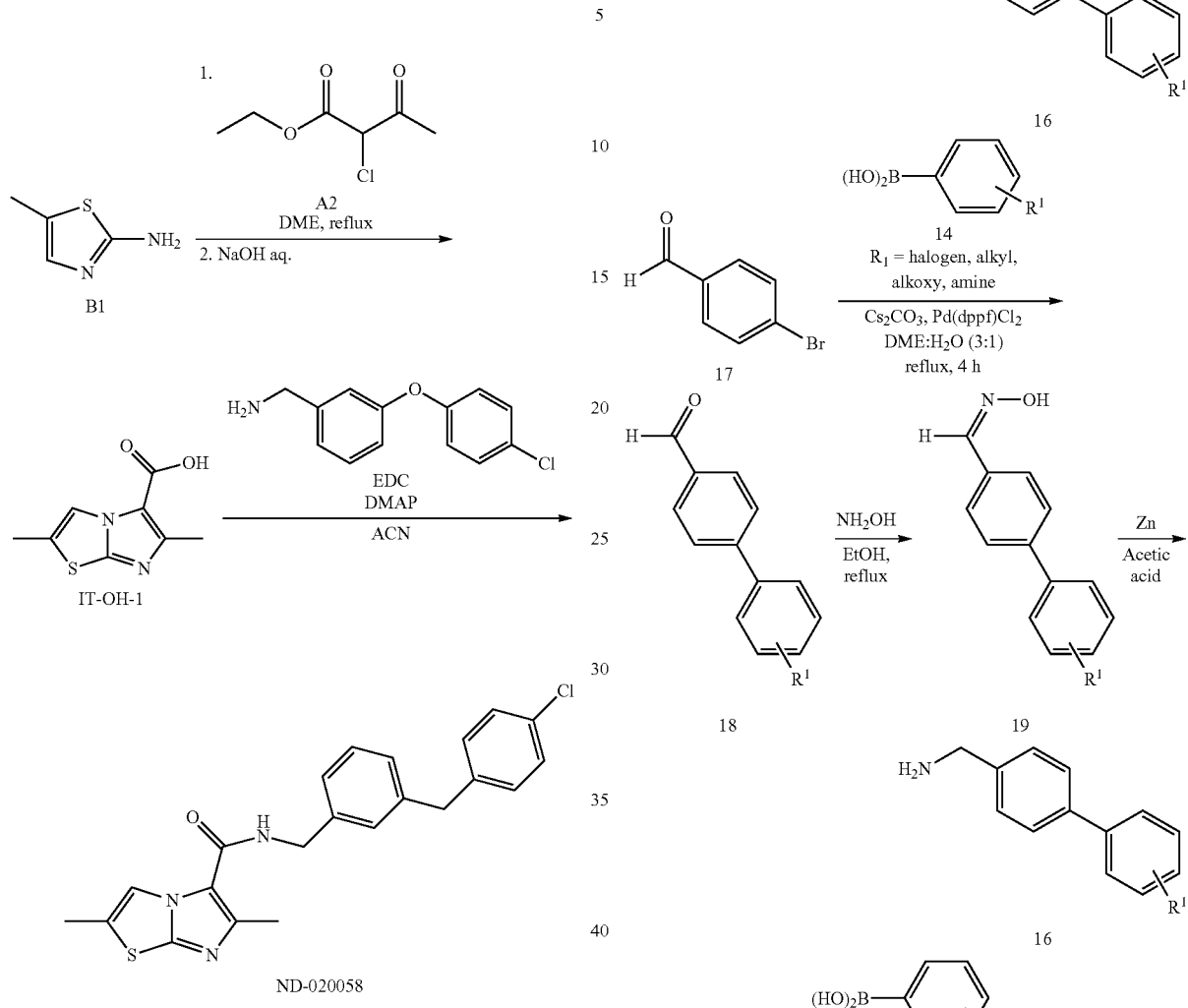

The general synthesis of substituted biaryl compounds 16 and 16'c:

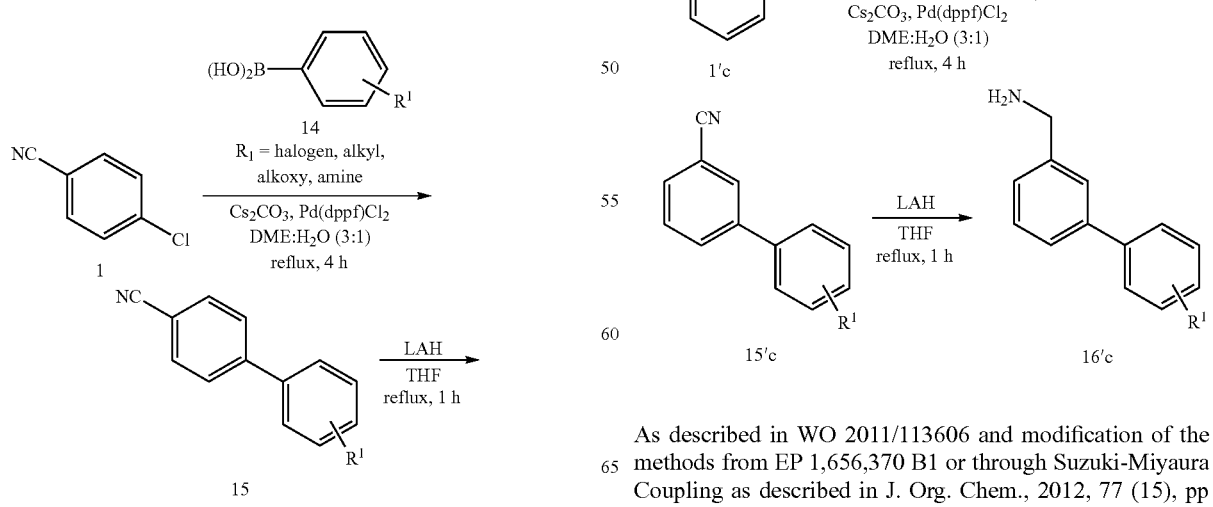

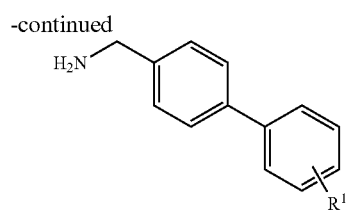

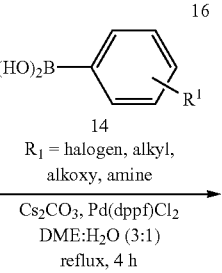

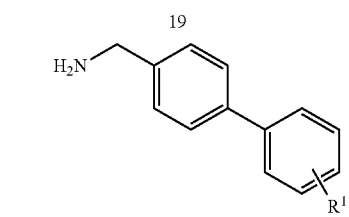

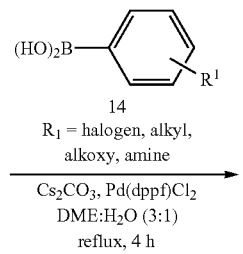

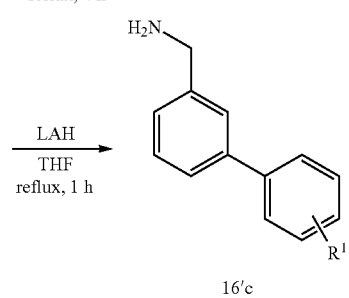

As described in WO 2011/113606 and modification of the methods from EP 1,656,370 B1 or through Suzuki-Miyaura Coupling as described in J. Org. Chem., 2012, 77 (15), pp 6608-6614; Applied Organometallic Chemistry, 2012, 26

Preparation of (4-(4-chlorophenoxy)phenyl)methanamine

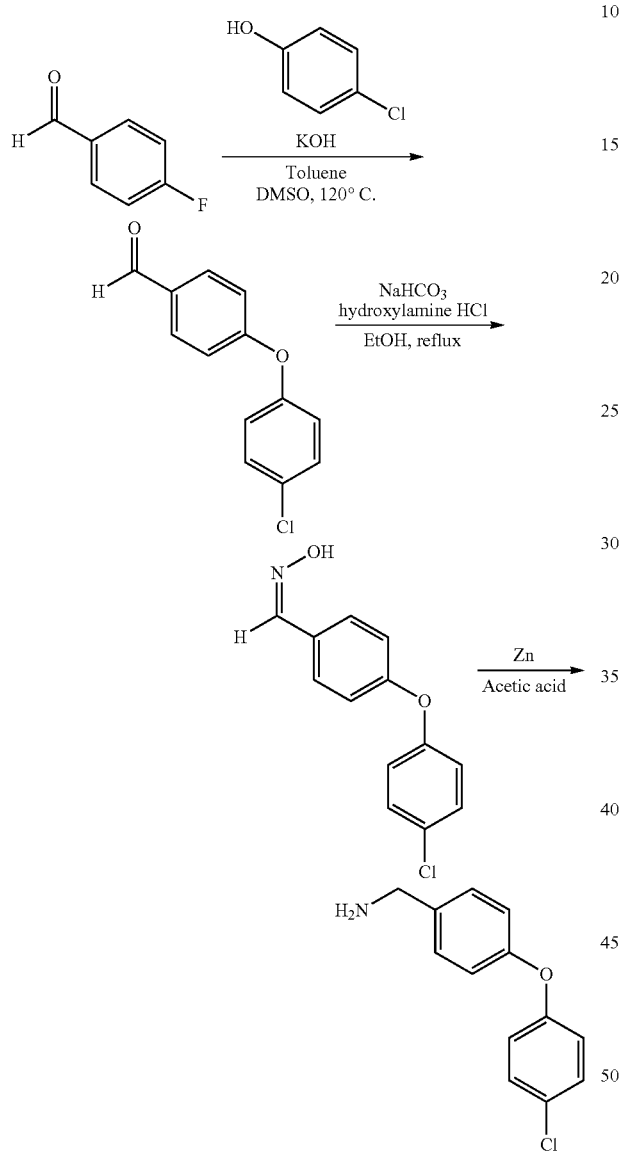

The 4-chlorophenol (173.4 mmol) and KOH (173.4 mmol) were dissolved in 22 mL DMSO and 100 mL toluene with a dean-stark trap. The reaction was heated to reflux (~120° C.) to drive off the water for 3 hours followed by collection of residual toluene. Once all water was collected the remaining toluene was removed and reaction temperature adjusted to 100° C. The 4-fluorobenzaldehyde (165.2 mmol) was added dropwise at 100° C. where it stirred for 12 h. At which time, the reaction mixture was cooled and poured over ice to precipitate product. Collect precipitate by filtration to collect 50.5 grams of 4-(4-chlorophenoxy)benzaldehyde.

4-(4-chlorophenoxy)benzaldehyde (3.2 mmol) and hydroxylamine hydrochloride (3.8 mmol) were combined in ethanol (7 mL). Then the sodium bicarbonate was added carefully (267 mg, 3.2 mmol) and the reaction mixture was heated to reflux for 2 h or upon completion by TLC. Reaction mixture was filtered hot to remove inorganic salts and filtrate liquor was concentrated to ⅓ volume. Upon standing solids formed and were collected by filtration to give 4-(4-chlorophenoxy)benzaldehyde oxime.

The 4-(4-chlorophenoxy)benzaldehyde oxime (20.2 mmol) was dissolved in acetic acid (40 mL) and then the zinc powder was added slowly (80.8 mmol) were it stirred at room temperature overnight. Reaction mixture was filtered to remove inorganic salts then evaporated to near dryness. The residue was suspending in dichloromethane and washed with aqueous NaOH solution until basic. The organic layer was filtered to collect the precipitate. Collected solids was dried over KOH under vacuum to give (4-(4-chlorophenoxy)phenyl)methanamine.

Compound of general structure 16 and 16'c can be elaborated to compounds like ND-02043 and the like through the following methods:

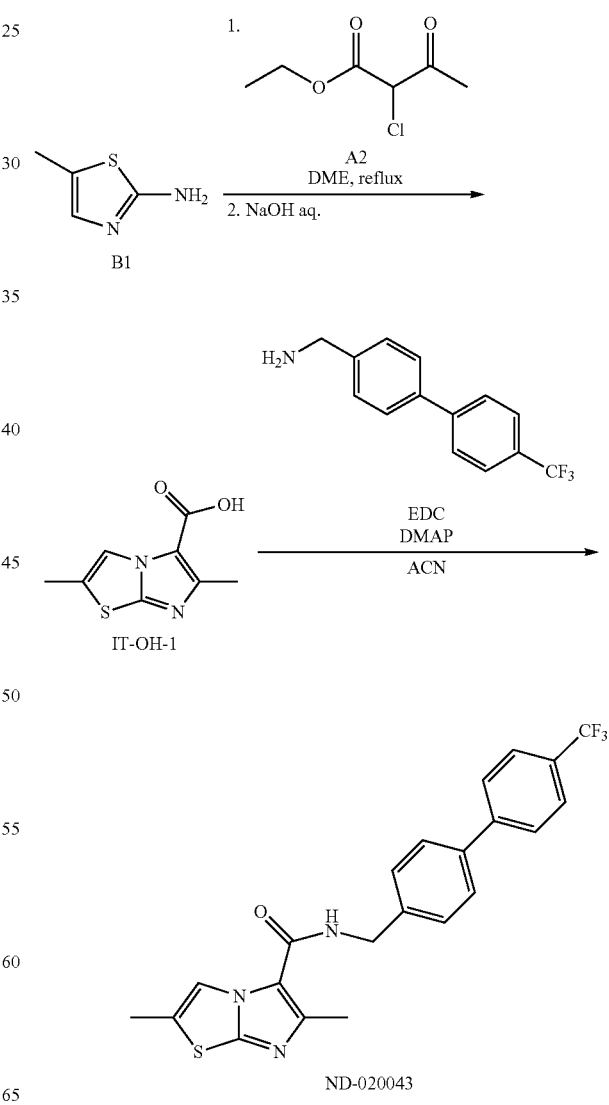

General synthesis of oxoacetamide compounds IT-O-A:

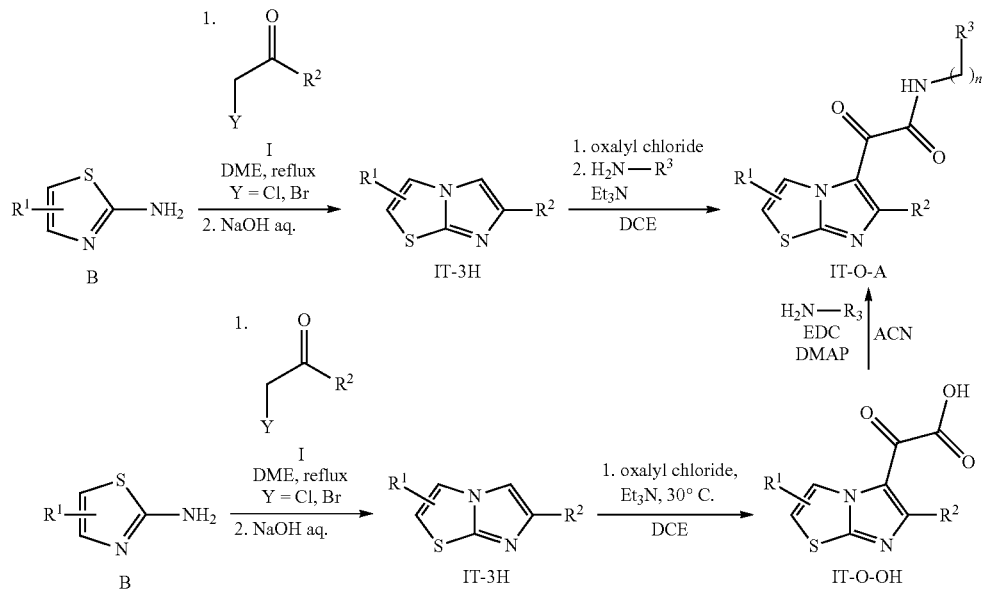

Amino-thiazole B (4.5 mmol) was dissolved in 10 ml of DCE (anhydrous) and cooled to 0° C. with an ice bath. Oxalyl chloride (5.8 mmol) in 3 mL of DCE (dry) was slowly added by addition funnel over 1 hour. Reaction was allowed to warm to room temperature where it stirred for 4 h. Triethylamine (5.8 mmol) in 5 mL DCE was slowly added over 15 mins and reaction stirred for 2.5 hours at 35° C. Then desired amine (5.4 mmol) was added and reaction remained at 35° C. overnight. Reaction concentrated down and then re-dissolved in DCM and washed with sat. NaHCO$_3$ sol (2×), acetic acid (2×), brine and then organics were dried over Na$_2$SO$_4$, filtered and concentrated to a brown semi-solid. Product (IT-O-A) was isolated by silica gel column with 30% EtOAC:DCM to collect major lower spot.

Reagents of formula I can also be prepared by the methods used for the synthesis of reagents of structure A but many are commercially available like ethyl chloroacetate or ethyl bromoacetate.

Alternatively, the oxoacetic acid (IT-O-OH) can be isolated prior to coupling with desired benzyl amines derivates to give desired products (IT-O-A). This is done by quenching with water and making basic with 25% NaOH, followed by extraction with DCE and adjusting the pH to 4-5 with acetic acid rather than just adding the desired amine for coupling. These methods were described in U.S. Pat. No. 8,183,377 B2 (Process for the preparation of imidazopyridines).

Additionally, the oxoacetic acid (IT-O-OH) can also be reduced by hydrazine hydrate and potassium hydroxide to give the acetic acid derivative (IT-CH2-OH) by the methods described in U.S. Pat. No. 8,183,377 B2 (Process for the preparation of imidazopyridines). The acetic acid derivative (IT-CH2-OH) can be reacted with benzyl amines by EDC mediated coupling to give the corresponding products of general structure IT-CH2-A.

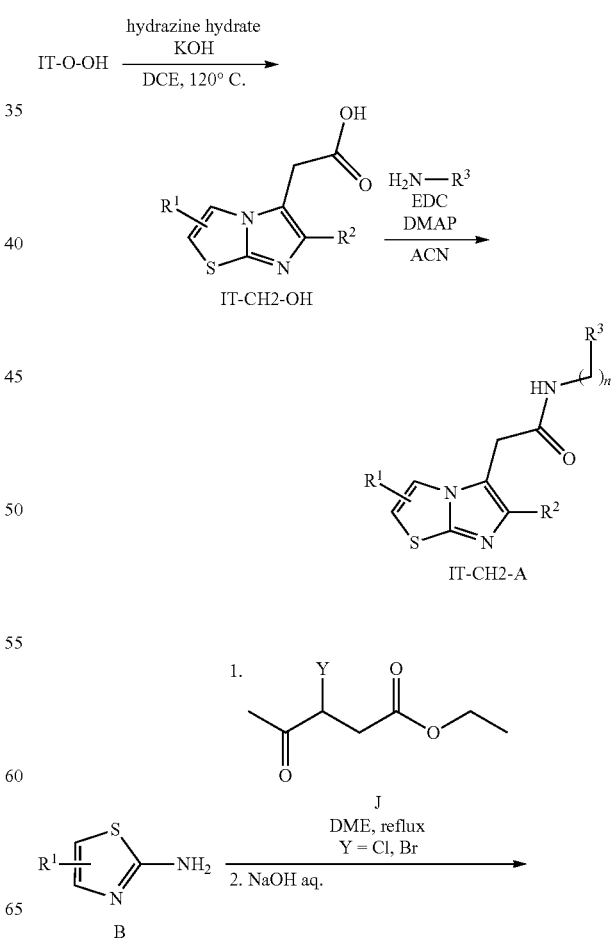

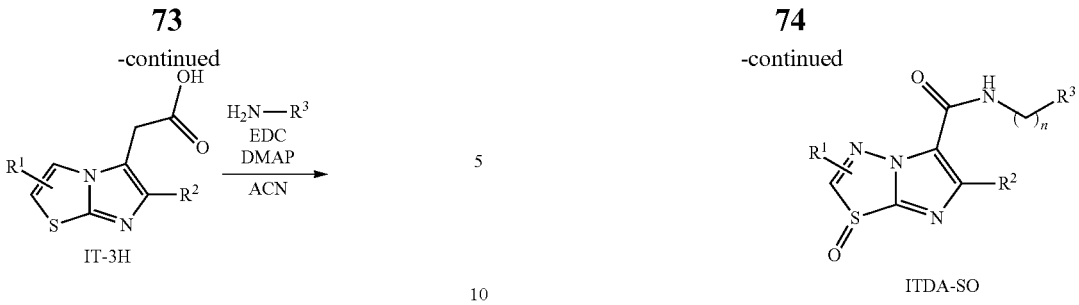

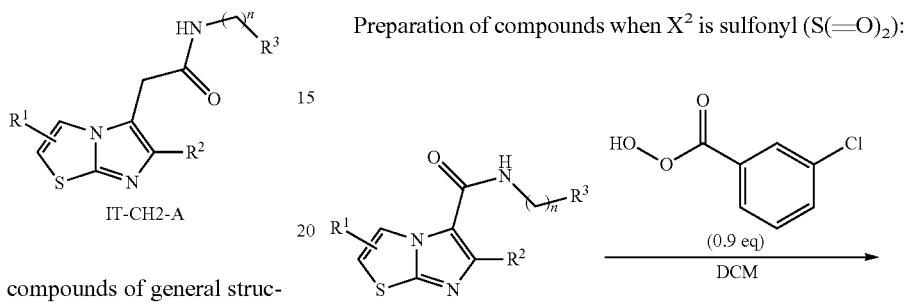

In a straightforward process compounds of general structure IT-CH2-A can be prepared by reaction of aminothiazole (B) with reagents of general structure J, followed by saponification and EDC-mediated coupling with desired amines by methods described previously (particularly the synthesis of ND-010081). Reagents of formula I can also be prepared by the methods used for the synthesis of reagents of structure A described previously.

Preparation of compounds when $X^2$ is sulfinyl (S(=O)):

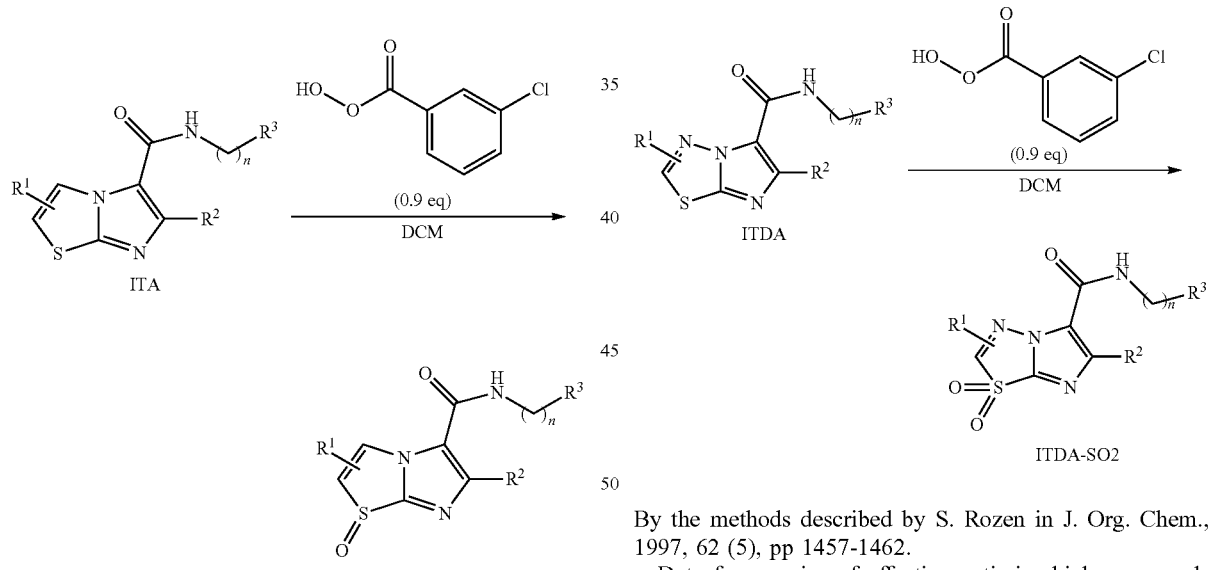

Preparation of compounds when $X^2$ is sulfonyl (S(=O)$_2$):

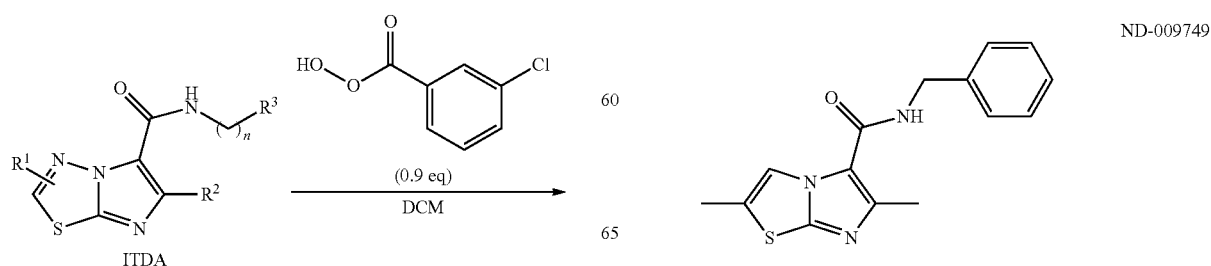

By the methods described by S. Rozen in J. Org. Chem., 1997, 62 (5), pp 1457-1462.

Data for a series of effective antimicrobial compounds prepared include the following, 1H NMR (300 MHz, CDCl₃) δ ppm 4.66 (2H, d, J=5.76 Hz), 2.56 (3H, s), 2.43 (3H, d, J=1.4 Hz), 7.99 (1H, m), 7.49-7.16 (5H, m)

ND-009763

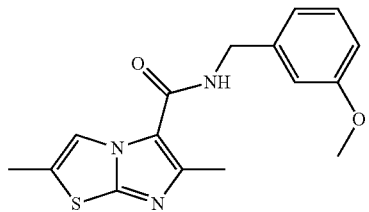

1H NMR (300 MHz, CDCl₃) δ ppm 4.64 (2H, d, J=5.7 Hz), 3.81 (3H, s), 2.57 (3H, s), 2.43 (3H, d, J=1.4 Hz), 7.06-6.75 (3H, m), 7.99 (1H, m), 7.32-7.24 (1H, m)

ND-009762

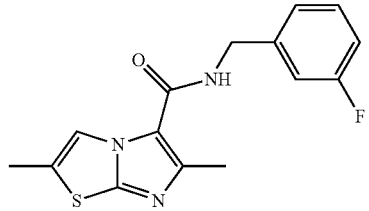

1H NMR (300 MHz, CDCl₃) δ ppm 4.66 (2H, d, J=5.8 Hz), 2.59 (3H, s), 2.43 (3H, d, J=1.3 Hz), 7.98 (1H, m), 7.32 (1H, m), 7.19-6.93 (3H, m).

ND-020006

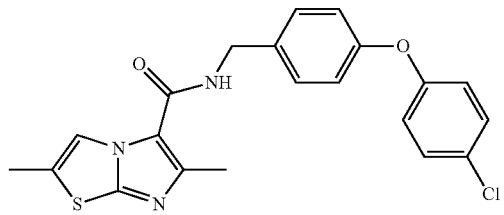

1H NMR (300 MHz, CDCl₃) δ ppm 4.69 (2H, d, J=6.0 Hz), 2.59 (3H, s), 2.43 (3H, d, J=1.3 Hz), 7.98 (1H, m), 7.28 (2H, d, J=8.0 Hz), 7.52 (2h, d, J=8.4 Hz).

ND-010081

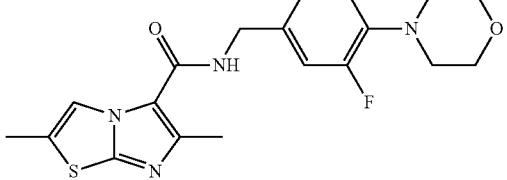

(300 MHz, CDCl3) δ ppm 4.62 (2H, d, J=5.8 Hz), 2.56 (3H, s), 2.43 (3H, d, J=1.3 Hz), 7.98 (1H, m), 7.31 (2H, d, J=8.7 Hz), 7.08-6.90 (6H, m).

ND-020060

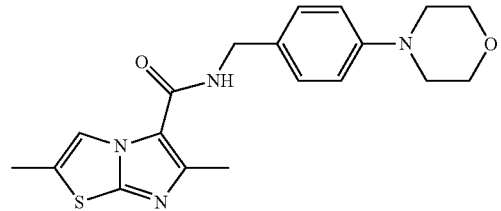

1H NMR (300 MHz, CDCl₃) δ ppm 4.64 (2H, d, J=5.7 Hz), 2.56 (3H, s), 2.44 (3H, d, J=1.3 Hz), 7.99 (1H, m), 7.32 (2H, d, J=8.7 Hz), 7.10-6.95 (6H, m)

ND-020033

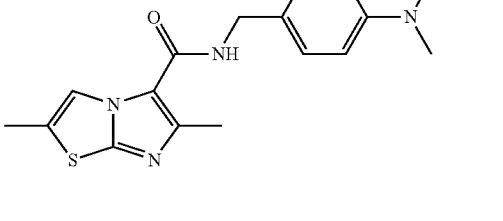

1H NMR (300 MHz, MeOH-d4) δ ppm 4.65 (2H, d, J=5.8 Hz), 2.54 (3H, s), 2.43 (3H, d, J=1.3 Hz), 3.14 (4H, t, J=4.8 Hz), 3.85 (4H, t, J=4.8 Hz), 7.98 (1H, m), 6.98 (2H, d, J=8.8 Hz), 7.32 (2h, d, J=8.8 Hz).

ND-020034

1H NMR (300 MHz, CDCl₃) δ ppm 4.64 (2H, d, J=5.9 Hz), 2.54 (3H, s), 2.43 (3H, d, J=1.3 Hz), 3.00-3.05 (4H, m), 3.83-3.87 (4H, m), 6.99 (1H, d J=8.0 Hz), 7.21 (dd, J=1.6, 8.0 Hz), 7.37 (1H, m), 7.99 (1H, m).

ND-020021

1H NMR (300 MHz, CDCl₃) δ ppm 4.68 (2H, d, J=5.6 Hz), 2.54 (3H, s), 2.46 (3H, d, J=1.4 Hz), 3.21-3.44 (6H, m), 7.99 (1H, m), 7.22-7.30 (2H, m), 6.56 (2H, d, J=8.4 Hz).

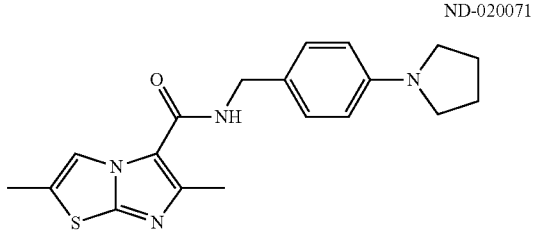 [SMILES: Cc1cn2c(C(=O)NCc3ccc(N4CCCC4)cc3)c(C)nc2s1]

ND-020071

1H NMR (300 MHz, CDCl$_3$) δ ppm 4.69 (2H, d, J=6.0 Hz), 1.99-2.04 (m, 4H), 3.29-3.38 (2H, m), 2.43 (3H, d, J=1.3 Hz), 7.98 (1H, m), 6.56 (2H, d, J=8.4 Hz), 7.14-7.31 (2H, m).

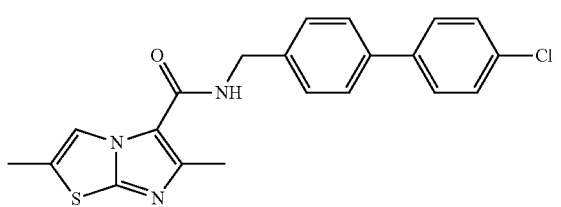 [SMILES: Cc1cn2c(C(=O)NCc3ccc(-c4ccc(Cl)cc4)cc3)c(C)nc2s1]

1H NMR (300 MHz, CDCl$_3$) δ ppm 4.65 (2H, d, J=5.76 Hz), 2.58 (3H, s), 2.43 (3H, d, J=1.4 Hz), 7.99 (1H, m), 7.49-7.16 (5H, m), 7.41 (2H, d, J=8.4 Hz), 7.45 (2H, d, J=8.0 Hz), 7.51 (2H, d, J=8.4 Hz), 7.57 (2H, d, J=8.0 Hz).

Example 3

Assays of Antimicrobial Activity

ND-010081, N-(4-(4-chlorophenoxy)benzyl)-2,6-dimethylimidazo[2,1-b]thiazole-5-carboxamide, an initial "hit" based on the 5,5-heteroaromatic scaffold described herein, has an in vitro activity against H$_{37}$Rv TB comparable to the current clinical candidates, and sufficient therapeutic window for in vivo treatment.

In accordance with various embodiments, Table 2 illustrates the potency of several exemplary compounds against M. Tuberculosis H$_{37}$Rv. In accordance with various embodiments, Table 3 illustrates the potency of several exemplary compounds against several clinical drug resistant strains of MDR- and XDR-M. tuberculosis.

TABLE 2

Potency of representative imidazo[2,1-b]thiazole against M. tuberculosis (Mtb) H$_{37}$Rv.

| Compound ID | M.W. | GAS media: replicating H$_{37}$Rv Mtb: MIC 90 (μM) | 7H12 media: Replicating H$_{37}$Rv Mtb: MIC 90 (μM) | VERO: IC$_{50}$ (μM) |
|---|---|---|---|---|
| ND-010081 | 395.45 | A | A | B |
| ND-010050 | 316.37 | B | C | E |
| ND-009763 | 315.39 | A | A | E |
| ND-009762 | 303.35 | A | A | E |
| ND-009749 | 285.36 | A | A | E |
| ND-009745 | 210.25 | E | E | E |
| ND-009744 | 224.28 | E | E | E |
| ND-009743 | 224.28 | E | E | E |
| ND-010475 | 287.34 | A | C | E |
| ND-020000 | 319.18 | A | A | E |
| ND-020001 | 319.18 | A | A | E |
| ND-020002 | 319.81 | A | A | E |

TABLE 2-continued

Potency of representative imidazo[2,1-b]thiazole against M. tuberculosis (Mtb) H$_{37}$Rv.

| Compound ID | M.W. | GAS media: replicating H$_{37}$Rv Mtb: MIC 90 (μM) | 7H12 media: Replicating H$_{37}$Rv Mtb: MIC 90 (μM) | VERO: IC$_{50}$ (μM) |
|---|---|---|---|---|
| ND-020003 | 321.35 | A | B | E |
| ND-020004 | 303.35 | A | A | E |
| ND-020005 | 321.35 | A | A | E |
| ND-020006 | 354.25 | A | A | E |
| ND-020007 | 369.36 | A | A | E |
| ND-020008 | 369.36 | A | A | E |
| ND-020009 | 353.36 | A | A | E |
| ND-020010 | 353.36 | A | A | E |
| ND-020011 | 367.39 | A | B | E |
| ND-020012 | 387.81 | A | A | E |
| ND-020013 | 373.78 | B | C | E |
| ND-020014 | 367.39 | A | B | E |
| ND-020015 | 373.78 | A | B | E |
| ND-020016 | 373.78 | A | A | E |
| ND-020017 | 388.8 | A | B | E |
| ND-020018 | 316.38 | A | A | E |
| ND-020019 | 327.4 | A | A | E |
| ND-020020 | 238.43 | A | A | E |
| ND-020021 | 238.43 | A | A | E |
| ND-020022 | 314.21 | A | A | E |
| ND-020023 | 248.85 | A | A | E |
| ND-020024 | 362.88 | A | B | E |
| ND-020025 | 382.4 | A | B | E |
| ND-020026 | 382.4 | A | A | E |
| ND-020027 | 342.46 | A | A | E |
| ND-020028 | 315.1 | A | A | E |
| ND-020029 | 329.42 | A | A | E |
| ND-020030 | 329.42 | A | A | E |
| ND-020031 | 343.44 | A | A | E |
| ND-020032 | 341.47 | A | B | E |
| ND-020033 | 370.47 | A | B | D |
| ND-020034 | 370.47 | A | B | E |
| ND-020035 | 388.46 | A | A | D |
| ND-020036 | 404.91 | A | B | E |
| ND-020037 | 371.46 | A | B | E |
| ND-020038 | 402.49 | B | B | E |
| ND-020039 | 442.43 | A | A | E |
| ND-020040 | 408.88 | A | A | E |
| ND-020041 | 431.33 | A | A | E |
| ND-020042 | 451.85 | A | B | E |
| ND-020043 | 415.43 | A | B | E |
| ND-020044 | 429.46 | B | B | E |
| ND-020045 | 416.42 | A | B | D |
| ND-020046 | 462.58 | A | A | C |
| ND-020047 | 476.61 | A | B | D |
| ND-020048 | 463.57 | A | A | C |
| ND-020049 | 477.6 | A | A | E |
| ND-020050 | 326.37 | A | B | D |
| ND-020051 | 378.4 | B | B | D |
| ND-020052 | 380.37 | A | B | D |
| ND-020053 | 396.44 | A | A | D |
| ND-020054 | 446.35 | A | A | D |
| ND-020055 | 459.48 | A | A | D |
| ND-020056 | 445.46 | A | B | E |
| ND-020057 | 323.77 | A | A | E |
| ND-020058 | 445.46 | A | A | D |
| ND-020059 | 411.9 | A | A | D |
| ND-020060 | 411.90 | A | A | C |
| ND-020061 | 399.41 | A | A | E |
| ND-020062 | 331.36 | A | A | E |
| ND-020063 | 347.82 | A | B | E |
| ND-020064 | 381.37 | A | A | D |
| ND-020065 | 351.43 | B | B | D |
| ND-020066 | 420.46 | A | B | D |
| ND-020067 | 434.49 | A | B | E |
| ND-020068 | 396.55 | A | A | E |
| ND-020069 | 396.55 | A | A | D |
| ND-020070 | 382.48 | A | B | D |
| ND-020071 | 354.47 | A | A | D |
| ND-020072 | 382.48 | A | A | E |
| ND-020073 | 354.47 | A | A | E |
| ND-020074 | 398.52 | A | A | D |

TABLE 2-continued

Potency of representative imidazo[2,1-b]thiazole against *M. tuberculosis* (Mtb) $H_{37}Rv$.

| Compound ID | M.W. | GAS media: replicating $H_{37}Rv$ Mtb: MIC 90 (μM) | 7H12 media: Replicating $H_{37}Rv$ Mtb: MIC 90 (μM) | VERO: $IC_{50}$ (μM) |
|---|---|---|---|---|
| ND-020075 | 398.52 | A | A | E |
| ND-020076 | 388.46 | A | A | E |
| ND-020077 | 338.43 | A | A | E |
| ND-020078 | 352.45 | A | A | E |
| ND-020079 | 338.43 | A | A | E |
| ND-020080 | 392.4 | A | A | E |
| ND-020081 | 333.07 | A | A | E |

Table 2 Activity Rankings:
A = ≤2 μM
B = <2 μM-10 μM
C = <10 μM-20 μM
D = <20 μM-32 μM
E = ≤32 μM GAS media is a growth media containing glycerol that is used to grow *M. tuberculosis* (Mtb) $H_{37}Rv$. 7H12 is a growth media that is used to grow *M. tuberculosis* (Mtb) $H_{37}Rv$ which does not containing glycerol as the carbon source. VERO is an assessment of toxicity to kidney epithelial cells extracted from an African green monkey.

TABLE 3

| Potency of a imidazo[2,1-b]thiazole against clinical MDR and XDR-Mtb strains. | | |
|---|---|---|
| | Compound $MIC_{90}$ μM (μg/mL) | |
| | ND-010081 | PA-824 |
| Drug sensitive Mtb clinical strain #1 | <0.01 (<0.025) | 0.45-0.86 (0.16-0.31) |
| Drug sensitive Mtb clinical strain #2 | <0.01 (<0.025) | >13.9 (>5) |
| MDR-TB resistant to HREZSKP | 0.02-10 (0.05-25) | 0.45-0.86 (0.16-0.31) |
| MDR-TB resistant to HREKP | <0.01 (<0.025) | 0.45-0.86 (0.16-0.31) |
| MDR-TB resistant to HRERb | 0.63 (1.6) | 0.45-0.86 (0.16-0.31) |
| XDR-TB resistant to HRESKO | <0.01 (<0.025) | 0.86 (0.31) |
| XDR-TB resistant to HREKO | <0.01 (<0.025) | 0.22 (0.08) |

MICs were done in 7H9/glucose/glycerol/BSA/0.05% Tween 80 and the average of three individual measurements. Abbreviations: H=isoniazid, R=rifampin, E=ethambutol, Z=pyrazinamide, S=streptomycin, K=kanamycin, P=para-aminosalicylic acid, Rb=rifabutin, O=oflxacin.

Description of TB (GAS[1], GAST[2], 7H12[1]) by Microplate Alamar Blue Assay (MABA) to Determine $MIC_{90}$ Values Against Replicating TB.

The test compound MICs against Mtb $H_{37}Rv$ (ATCC#27294) were assessed by the MABA using rifampin and PA-824 as positive controls. Compound stock solutions were prepared in DMSO at a concentration of 128 μM, and the final test concentrations ranged from 128 μM to 0.5 μM. Two fold dilutions of compounds were prepared in glycerol-alanine-salt media in a volume of 100 μL in 96-well microplates (BD Optilux™, 96-well Microplates, black/clear flat bottom) for the GAS assay, in an iron deficient glycerol-alanine-salt media with 20% Tween 80 added in the GAST assay and in Middlebrook 7H12 medium (7H9 broth containing 0.1% w/v casitone, 5.6 μg/mL palmitic acid, 5 mg/mL bovine serum albumin, 4 mg/mL catalase) in a volume of 100 μL in 96-well microplates (BD Optilux™, 96-well Microplates, black/clear flat bottom) for the 7H12 assay. The TB cultures (100 μL inoculums of 2×105 cfu/mL) were added to the media, yielding a final testing volume of 200 μL. The plates were incubated at 37° C. On the seventh day of incubation, 12.5 μL of 20% Tween 80, and 20 μL of Alamar Blue (Invitrogen BioSource™) were added to the wells of test plate. After incubation at 37° C. for 16-24 h, fluorescence of the wells was measured at 530 nm (excitation) and 590 nm (emmision). The MICs are defined as the lowest concentration effecting a reduction in fluorescence of ≥90% relative to the mean of replicate bacteria-only controls.

Citations for information regarding the assays described above.

1. Collins, L.; Franzblau, S. G. Microplate alamar blue assay versus BACTEC 460 system for high-throughput screening of compounds against *Mycobacterium tuberculosis* and *Mycobacterium avium. Antimicrob. Agents Chemother.* 1997, 41, 1004-1009.
2. De Voss, J. J.; Rutter, K.; Schroeder, B. G.; Su, H.; Zhu, Y.; Barry, C. E. The salicylate-derived mycobactin siderophores of *Mycobacterium tuberculosis* are essential for growth in macrophages. *Proc. Nat. Acad. Sci. U.S.A.* 2000, 97, 1252-1257.

Example 4

Pharmaceutical Compositions and Dosage Forms

The following formulations illustrate representative pharmaceutical dosage forms that may be used for the therapeutic or prophylactic administration of a compound of a formula described herein, a compound specifically disclosed herein, or a pharmaceutically acceptable salt or solvate thereof (hereinafter referred to as 'Compound X'):

| (i) Tablet 1 | mg/tablet |
|---|---|
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| 'Compound X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| 'Compound X' | 10.0 |
| Colloidal silicon dioxide | 1.5 |
| Lactose | 465.5 |
| Pregelatinized starch | 120.0 |
| Magnesium stearate | 3.0 |
| | 600.0 |

-continued

| (iv) Injection 1 (1 mg/mL) | mg/mL |
|---|---|
| 'Compound X' (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/mL) | mg/mL |
|---|---|
| 'Compound X' (free acid form) | 10.0 |
| Monobasic sodium phosphate | 0.3 |
| Dibasic sodium phosphate | 1.1 |
| Polyethylene glycol 400 | 200.0 |
| 0.1N Sodium hydroxide solution (pH adjustment to 7.0-7.5) | q.s. |
| Water for injection | q.s. ad 1 mL |

| (vi) Aerosol | mg/can |
|---|---|
| 'Compound X' | 20 |
| Oleic acid | 10 |
| Trichloromonofluoromethane | 5,000 |
| Dichlorodifluoromethane | 10,000 |
| Dichlorotetrafluoroethane | 5,000 |

| (vii) Topical Gel 1 | wt. % |
|---|---|
| 'Compound X' | 5% |
| Carbomer 934 | 1.25% |
| Triethanolamine (pH adjustment to 5-7) | q.s. |
| Methyl paraben | 0.2% |
| Purified water | q.s. to 100 g |

| (viii) Topical Gel 2 | wt. % |
|---|---|
| 'Compound X' | 5% |
| Methylcellulose | 2% |
| Methyl paraben | 0.2% |
| Propyl paraben | 0.02% |
| Purified water | q.s. to 100 g |

| (ix) Topical Ointment | wt. % |
|---|---|
| 'Compound X' | 5% |
| Propylene glycol | 1% |
| Anhydrous ointment base | 40% |
| Polysorbate 80 | 2% |
| Methyl paraben | 0.2% |
| Purified water | q.s. to 100 g |

| (x) Topical Cream 1 | wt. % |
|---|---|
| 'Compound X' | 5% |
| White bees wax | 10% |
| Liquid paraffin | 30% |
| Benzyl alcohol | 5% |
| Purified water | q.s. to 100 g |

| (xi) Topical Cream 2 | wt. % |
|---|---|
| 'Compound X' | 5% |
| Stearic acid | 10% |
| Glyceryl monostearate | 3% |
| Polyoxyethylene stearyl ether | 3% |
| Sorbitol | 5% |
| Isopropyl palmitate | 2% |
| Methyl Paraben | 0.2% |
| Purified water | q.s. to 100 g |

These formulations may be prepared by conventional procedures well known in the pharmaceutical art. It will be appreciated that the above pharmaceutical compositions may be varied according to well-known pharmaceutical techniques to accommodate differing amounts and types of active ingredient 'Compound X'. Aerosol formulation (vi) may be used in conjunction with a standard, metered dose aerosol dispenser. Additionally, the specific ingredients and proportions are for illustrative purposes. Ingredients may be exchanged for suitable equivalents and proportions may be varied, according to the desired properties of the dosage form of interest.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A compound of Formula (A):

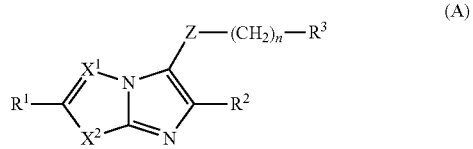

(A)

wherein
$X^1$ is CH;
$X^2$ is S;
Z is —C(=O)NH—;
n is 1 to 4;
$R^1$ is $C_{1-6}$ alkyl, halo, or trifluoromethyl;
$R^2$ is $C_{1-6}$ alkyl, or trifluoromethyl;
$R^3$ is
(a) $OR^4$ or $NHR^4$;
(b)

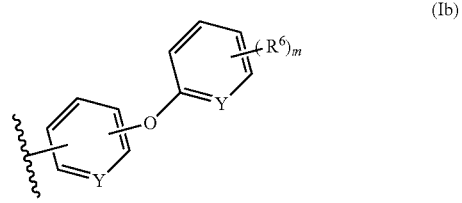

(Ib)

wherein each Y is independently CH or N; $R^6$ is H, $CF_3$, $OCF_3$, halo, methylsulfone, alkoxy, amine, or nitrile; and m is 1-4;

(c)

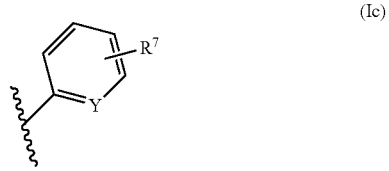

(Ic)

wherein Y is CH or N; and $R^7$ is a heterocycle, wherein the heterocycle is an optionally substituted furan, thiophene, imidazole, oxazole, oxazoline, oxadiazole, thiadiazole, thiazole, thiazoline, triazole, pyridine, pyrazine, pyrazole, diketopiperazine, quinoline, isoquinoline, or oxazolindinone;

(d)

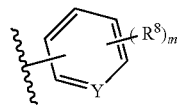
(Id)

wherein Y is CH or N; and $R^8$ is $CF_3$, $OCF_3$, halo, methylsulfone, nitrile, or optionally substituted alkoxy, amine, phenyl, or heterocycle; and m is 0-3;

(e)

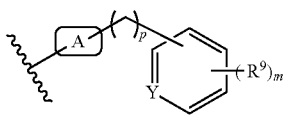
(Ie)

wherein A is a heterocycle, wherein the heterocycle is a furan, a thiophene, an imidazole, an oxazole, an oxazoline, an oxadiazole, a thiadiazole, a thiazole, a thiazoline, a triazole, a pyridine, a pyrazine, a diketopiperazine, a quinoline, an isoquinoline, a benzimidazole, a benzoxazole, a benzthiazole or an oxazolindinone; $R^9$ is $CF_3$, $OCF_3$, halo, methylsulfone, alkoxy, amine or nitrile; Y is CH or N; m is 0-5; and p is 0-4;

(f)

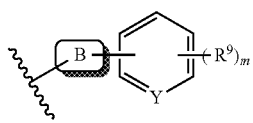
(If)

wherein B is a heterocycle, wherein the heterocycle is a piperazine or a piperidine; $R^9$ is $CF_3$, $OCF_3$, halo, methylsulfone, alkoxy, amine, or nitrile; Y is CH or N; and m is 0-4;

(g)

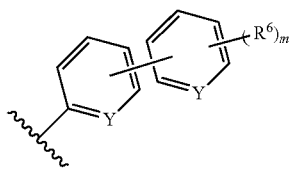
(Ig)

wherein each Y is independently CH or N; $R^6$ is $CF_3$, $OCF_3$, halo, methylsulfone, alkoxy, amine or nitrile; and m is 0-4; or (h)

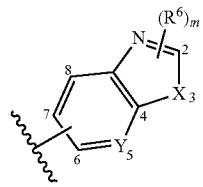
(Ih)

wherein the structure (Ih) is connected to the structure of Formula A at position 2, 6, or 7; $R^6$ when present is located at position 2, 6, or 7, or a combination thereof, provided that structure (Ih) is not connected to the structure of Formula A at the same position; X is $CH_2$, NH, $NR_4$, S, or O; Y is CH or N; $R^6$ is $CF_3$, $OCF_3$, halo, methylsulfone, alkoxy, amine or nitrile; and m is 0-3;

each $R^4$ is independently alkyl, cycloalkyl, heterocycle, aryl, or heteroaryl; and wherein any alkyl, cycloalkyl, heterocycle, aryl, aryloxy, heteroaryl, alkoxy, or amine of $R^3$ or $R^4$ is optionally substituted with one to five substituents;

or a pharmaceutically acceptable salt thereof.

2. The compound of claim 1 wherein $R^1$ is methyl, trifluoromethyl, chloro, or fluoro.

3. The compound of claim 1 wherein $R^2$ is methyl, trifluoromethyl, or ethyl.

4. The compound of claim 1 wherein the compound is N-(4-(4-chlorophenoxy)benzyl)-2,6-dimethylimidazo[2,1-b]thiazole-5-carboxamide (ND-010081).

5. A composition comprising a compound of claim 1 in combination with a pharmaceutically acceptable diluent or carrier.

6. A method of killing or inhibiting the growth of *M. tuberculosis* bacteria comprising contacting the bacteria with an effective lethal or inhibitory amount of a compound of claim 1.

7. A method of therapeutically treating *M. tuberculosis* bacterial infection in a subject having the infection, comprising administering a compound of claim 1 to the subject.

8. A method of therapeutically treating *M. tuberculosis* bacterial infection in a subject having the infection, comprising administering a composition of claim 5 to the subject.

9. The compound of claim 1, wherein n is 1.
10. The compound of claim 1, wherein n is 2.
11. The compound of claim 1, wherein $R^1$ is $C_{1-6}$ alkyl.
12. The compound of claim 1, wherein $R^1$ is methyl.
13. The compound of claim 1, wherein $R^1$ is halo.
14. The compound of claim 1, wherein $R^1$ is chloro.
15. The compound of claim 1, wherein $R^1$ is fluoro.
16. The compound of claim 1, wherein $R^1$ is trifluoromethyl.
17. The compound of claim 1, wherein $R^2$ is $C_{1-6}$ alkyl.
18. The compound of claim 1, wherein $R^2$ is methyl.
19. The compound of claim 1, wherein $R^2$ is ethyl.
20. The compound of claim 1, wherein $R^2$ is trifluoromethyl.

* * * * *